(12) United States Patent
Huang et al.

(10) Patent No.: US 8,734,867 B2
(45) Date of Patent: *May 27, 2014

(54) ANTIBACTERIAL HAVING AN EXTRACT OF POMEGRANATE COMBINED WITH HYDROGEN PEROXIDE

(75) Inventors: Alexander L. Huang, Menlo Park, CA (US); Gin Wu, San Rafael, CA (US)

(73) Assignee: Liveleaf, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/317,638

(22) Filed: Dec. 23, 2008

(65) Prior Publication Data
US 2011/0070198 A1    Mar. 24, 2011

Related U.S. Application Data (60) Provisional application No. 61/009,484, filed on Dec. 28, 2007.

(51) Int. Cl.
*A61K 36/00*    (2006.01)

(52) U.S. Cl.
USPC .......................... 424/777; 424/729; 424/725

(58) Field of Classification Search
USPC .......................................... 424/777, 729, 725
See application file for complete search history.

(56) References Cited

U.S. PATENT DOCUMENTS

| | | |
|---|---|---|
| 1,844,018 A | 12/1929 | Sailer |
| 1,891,149 A | 11/1931 | Elger |
| 1,965,458 A | 7/1934 | Elger .......................... 260/137 |
| 3,484,248 A | 12/1969 | Nathaniel et al. |
| 3,649,297 A | 3/1972 | Millin |
| 3,692,904 A | 9/1972 | Tsutsumi ...................... 424/227 |
| 3,817,835 A | 6/1974 | Neidleman ................. 195/80 R |
| 3,821,440 A | 6/1974 | Revee |
| 3,824,184 A | 7/1974 | Hatcher et al. .................... 210/1 |

(Continued)

FOREIGN PATENT DOCUMENTS

| | | |
|---|---|---|
| CN | 200910167930 | 10/2009 |
| EP | 0390107 | 10/1990 |

(Continued)

OTHER PUBLICATIONS

MacPhillamy, HB; Drugs From Plants; Plant Science Bulletin; vol. 9, Apr. 1963, No. 2, pp. 1-15.*

(Continued)

*Primary Examiner* — Patricia Leith
(74) *Attorney, Agent, or Firm* — Brian S. Boyer; Syndicated Law, PC (57) ABSTRACT

The present invention is directed to a method and a composition for producing and using a plant-based biocidal solution. The plant-based biocidal solution contains a bioactive material and a plant-based substance formed from the cellular material of a plant. The plant-based substance is capable of binding to the bioactive material. In some embodiments, the bioactive material is hydrogen peroxide. The hydrogen peroxide can be added exogenously or generated endogenously. In accordance with further embodiments, the plant-based biocidal solution can be applied to a target, thereby impairing the target. In some embodiments, the target can be a pathogen. In accordance with another embodiment, the plant-based substance of the plant-based biocidal solution can form a microscopic cluster, a complex, or an aggregate for providing sufficient bioactive material to overcome the defense mechanism of the target.

11 Claims, 4 Drawing Sheets

(56) References Cited

U.S. PATENT DOCUMENTS

| | | | |
|---|---|---|---|
| 3,860,694 A | 1/1975 | Jayawant | |
| 3,864,454 A | 2/1975 | Pistor et al. | |
| 4,008,339 A | 2/1977 | Matsuda et al. | 426/330.4 |
| 4,072,671 A | 2/1978 | Sodini et al. | 260/123.5 |
| 4,171,280 A | 10/1979 | Maddox et al. | |
| 4,435,601 A | 3/1984 | Formanek et al. | 568/430 |
| 4,472,302 A | 9/1984 | Karkhanis | 260/112 |
| 4,472,602 A | 9/1984 | Bordelon et al. | |
| 4,514,334 A | 4/1985 | Mark | 260/395 |
| 4,623,465 A | 11/1986 | Klibanov | 210/632 |
| 4,829,001 A | 5/1989 | Mencke et al. | 435/264 |
| 4,900,671 A | 2/1990 | Pokora et al. | 435/156 |
| 4,966,762 A | 10/1990 | Pfeffer et al. | |
| 5,141,611 A | 8/1992 | Ford | 204/182.4 |
| 5,208,010 A | 5/1993 | Thaler | 424/53 |
| 5,231,193 A | 7/1993 | Mizusawa et al. | 549/278 |
| 5,260,021 A | 11/1993 | Zeleznick | |
| 5,296,376 A | 3/1994 | Bridges et al. | 435/320 |
| 5,328,706 A | 7/1994 | Endico | 426/231 |
| 5,389,369 A | 2/1995 | Allen | |
| 5,614,501 A | 3/1997 | Richards | 514/22 |
| 5,653,746 A | 8/1997 | Schmitt | |
| 5,661,170 A | 8/1997 | Chodosh | 514/390 |
| 5,700,769 A | 12/1997 | Schneider et al. | 510/305 |
| 5,756,090 A | 5/1998 | Allen | |
| 5,824,414 A | 10/1998 | Kobayashi et al. | 428/402 |
| 5,834,409 A * | 11/1998 | Ramachandran et al. | 510/125 |
| 5,839,369 A | 11/1998 | Chatterjee et al. | |
| 5,879,733 A | 3/1999 | Ekanayake et al. | 426/271 |
| 5,891,440 A * | 4/1999 | Lansky | 424/727 |
| 6,068,862 A | 5/2000 | Ishihara et al. | |
| 6,080,573 A | 6/2000 | Convents et al. | 435/263 |
| 6,136,849 A | 10/2000 | Hoffmann et al. | 514/456 |
| 6,284,770 B1 | 9/2001 | Mangel et al. | |
| 6,383,523 B1 | 5/2002 | Murad | |
| 6,420,148 B2 | 7/2002 | Yamaguchi | 435/189 |
| 6,436,342 B1 | 8/2002 | Petri et al. | |
| 6,444,805 B1 | 9/2002 | Sohn et al. | 536/23.72 |
| 6,537,546 B2 | 3/2003 | Echigo et al. | |
| 6,551,602 B1 | 4/2003 | Barrett et al. | 424/401 |
| 6,630,163 B1 * | 10/2003 | Murad | 424/464 |
| 6,642,277 B1 | 11/2003 | Howard et al. | 514/783 |
| 6,926,881 B2 | 8/2005 | Hirose et al. | |
| 7,018,660 B2 | 3/2006 | Murad | |
| 7,241,461 B2 | 7/2007 | Myhill et al. | |
| 7,297,344 B1 | 11/2007 | Fleischer et al. | |
| 7,341,744 B1 | 3/2008 | Rozhon et al. | |
| 7,504,251 B2 | 3/2009 | Olshenitsky et al. | 435/252.8 |
| 8,067,041 B2 | 11/2011 | Quart et al. | |
| 2001/0007762 A1 | 7/2001 | Echigo et al. | |
| 2002/0034553 A1 | 3/2002 | Zayas | |
| 2002/0041901 A1 | 4/2002 | Murad | |
| 2002/0172719 A1 | 11/2002 | Murad | |
| 2003/0078212 A1 | 4/2003 | Li et al. | |
| 2004/0137077 A1* | 7/2004 | Ancira et al. | 424/616 |
| 2004/0228831 A1 | 11/2004 | Belinka, Jr. et al. | |
| 2005/0169988 A1 | 8/2005 | Tao et al. | |
| 2006/0024339 A1 | 2/2006 | Murad | |
| 2006/0024385 A1 | 2/2006 | Pedersen | |
| 2006/0051429 A1 | 3/2006 | Murad | |
| 2006/0165812 A1 | 7/2006 | Charron | |
| 2007/0010632 A1 | 1/2007 | Kaplan et al. | |
| 2007/0110812 A1* | 5/2007 | Xia et al. | 424/487 |
| 2007/0154414 A1 | 7/2007 | Bonfiglio | |
| 2008/0003314 A1 | 1/2008 | Ochiai et al. | |
| 2008/0118602 A1 | 5/2008 | Narayanan et al. | |
| 2009/0023804 A1 | 1/2009 | Baugh et al. | |
| 2009/0048312 A1 | 2/2009 | Greenberg et al. | 514/367 |
| 2009/0083885 A1 | 3/2009 | Daniell | 800/312 |
| 2009/0093440 A1 | 4/2009 | Murad | |
| 2010/0055138 A1 | 3/2010 | Margulies et al. | |
| 2010/0158885 A1 | 6/2010 | Huang et al. | |
| 2010/0278759 A1 | 11/2010 | Murad | |
| 2011/0052557 A1 | 3/2011 | Huang et al. | |
| 2011/0070198 A1 | 3/2011 | Huang et al. | |
| 2013/0078322 A1 | 3/2013 | Huang et al. | |

FOREIGN PATENT DOCUMENTS

| | | | |
|---|---|---|---|
| EP | 0797451 | 9/2004 | |
| EP | 0797451 B1 | 9/2004 | A61K 45/06 |
| EP | 1736165 | 12/2006 | |
| EP | 1736165 A1 | 12/2006 | A61K 35/74 |
| WO | WO/94/03607 | 2/1994 | |
| WO | WO200403607 | 2/1994 | C12N 15/53 |
| WO | WO 00/06116 | 2/2000 | |
| WO | WO 2004/003607 | 1/2004 | |
| WO | WO 2005/067727 | 7/2005 | |
| WO | WO 2005/099721 | 10/2005 | |
| WO | WO 2006/038893 | 4/2006 | |
| WO | WO2006038893 | 4/2006 | C07B 41/02 |
| WO | WO 2006/096778 | 11/2006 | |
| WO | WO 2007/003068 | 1/2007 | |
| WO | WO 2010/018418 | 2/2010 | |
| WO | WO 2010/101844 | 9/2010 | |
| WO | WO 2012/178127 | 1/2013 | |

OTHER PUBLICATIONS

Raskin et al. Can an Apple a Day Keep the Doctor Away? Current Pharmaceutical Design, 2004, 10, 3419-3429.*

Webster's Online Dictionary: Prophylactic; Online, URL<http://www.merriam-webster.com/dictionary/prophylactic> accessed Mar. 6, 2014, 3 pages.*

Patent Cooperation Treaty, "Notification of Transmittal of the International Search Report and the Written Opinion of the International Searching Authority, or the Declaration", International Application No. PCT/US10/25805, Date of Mailing: Apr. 23, 2010, International Filing Date: Mar. 1, 2010, Applicant: MetaActiv, Inc.

Asquith, T.N., et al., Interactions of Condensed Tannins with Selected Proteins, *Phytochemistry*, 1986, 25: 1591-1593.

Avdiushko, S.A., et al., Detection of Several Enzymatic Activities in Leaf Prints of Cucumber Plant, *Physiological and Molecular Plant Pathology*, 1993, 42: 441-454.

Baeuerle, P.A., Reactive Oxygen Intermediates as Second Messengers of a General Pathogen Response, *Pathol Biol.* 1996, 44(1): 29-35.

Barroso, J.B., et al., Localization of Nitric-oxide Synthase in Plant Peroxisomes, *The Journal of Biological Chemistry*, 1999, 274(51): 36729-36733.

Berglin, E.H., et al., Potentiation by L-Cysteine of the Bactericidal Efffect of Hydrogen Peroxide in *Escherichia coli*, *J. Bacteriol.*, 1982, 152(1): 81-88.

Berglin, E. H., et al., Potentiation by Sulfide of Hydrogen Peroxide-Induced Killing of *Escherichia coli*, *Infection and Immunity*, 1985, 49(3): 538-543.

Bernays, E.A., et al., Herbivores and Plant Tannins, *Advances in Ecological Research*, 1989, 19: 263-302.

Bowditch, M.I., et al., Ascorbate Free-Radical Reduction by Glyoxysomal Membranes, *Plant Physiology*, 1990, 94: 531-537.

Bowler, C., et al., Superoxide Dismutase and Stress Tolerance, *Annu. Rev. Plant Physiol. Plant Mol. Biol.*, 1992, 43: 83-116.

Bowler, C., et al., Superoxide Dismutase in Plants, *Crit. Rev. Plant Sci.*, 1994, 13(3): 199-218.

Breusegem, F.V., et al., The Role of Active Oxygen Species in Plant Signal Transduction, *Plant Science*, 2001, 161: 405-414.

Buchanan-Wollaston, V., The Molecular Biology of Leaf Senescence, 1997, *J. Ex. Bot.* 48(2): 181-199.

Bunkelmann, J.R., et al., Ascorbate Peroxidase. A Prominent Membrane Protein in Oilseed Glyoxysomes, 1996, *Plant Physiol.*, 110(2): 589-598.

Butler, E., et al., The role of Lysyl Oxidase and Collagen Crosslinking During Sea Urchin Development, *Exp. Cell Res.*, 1987, 173: 174-182.

Butler, L.G., et al., Interaction of Proteins with Sorghum Tannin: Mechanism, Specificity and Significance, *Journal of the American Oil Chemists' Society*, 1984, 61(5): 916-920.

(56) References Cited

OTHER PUBLICATIONS

Cheng, H.Y., et al., Antiherpes Simplex Virus Type 2 activity of of Casuarinin from the Bark of Terminalia Arjuna Linn, *Antiviral Research*, 2002, 55(3): 447-455.

Cordeiro, C., et al., Antibacterial Efficacy of Gentamicin encapsulated in pH-Sensitive Liposomes against an In Vivo *Salmonella enteric* Serovar Typhimurium Intracelllular Infection Model, *Antimicrobial agents and Chemotherapy*, 2000, 44(3): 533-539.

Corpas, F.J., et al., A Role for Leaf Peroxisomes in the Catabolism of Purines, 1997, *J. Plant Physiol.*, 151: 246-250.

Corpas, F.J., et al., Copper-Zinc Superoxide Dismutase is a Constituent Enzyme of the Matrix of Peroxisomes in the Cotyledons of Oilseed Plants, *New Phytol.*, 1998, 138(2): 307-314.

De Paepe, K., et al., Repair of Acetone- and Sodium Lauryl Sulphate-damaged Human Skin Barrier Function Using Topically Applied Emulsions Containing Barrier Lipids, *Journal of European Academy of Dermatology & Venereology*, 2002, Nov. 2002, 1 pg.

Del Río, L.A., et al., Metabolism of Oxygen Radicals in Peroxisomes and Cellular Implications, *Free Radical Biol. Med.*, 1992, 13(5): 557-580.

Del Río, L.A., et al., Peroxisomes as a Source of Superoxide and Hydrogen Peroxide in Stressed Plants, *Biochem. Soc. Trans.*, 1996, 24: 434-438.

Del Rio, L.A., Physiol., et al., The Activated Oxygen Role of Peroxisomes in Senescence, *Plant Physiol.*, 1998, 116(4): 1195-1200.

Doke, N., et al., The Oxidative Burst Protects Plants Against Pathgen Attack: Mechanism and Role as an Emergency Signal for Plant Bio-Defence, *Gene*, 1996, 179(1): 45-51.

El Amin, F.M., et al., Genetic and Environmental Effects upon Reproductive Performance of Holstein Crossbreds in the Sudan, *Dairy Sci.*, 1986, 69: 1093-1097.

Elstner, E.F., et al., Mechanisms of Oxygen Activation During Plant Stress, *Proceedings of the Royal Society of Edinburgh B Biology*, 1994, 102B, 131-154.

Fang, T.K., et al., Electron Transport in Purified Glyoxysomal Membranes from Castor Bean Endosperm, *Planta*, 1987, 172(1): 1-13.

Fridovich, I., Superoxide Dismutases, 1986, *Adv. Enzymol. Relat. Areas Mol. Biol.*, 58: 61-97.

Funatogawa, K., et al., Antibacterial Activity of Hydrolysable Tannins Derived from Medicinal Plants against *Helicobacter pylori*, *Microbiol. Immunol.*, 2004, 48(4): 251-261.

Gallily, R., et al., Non-immunological Recognition and Killing of Xenogeneic Cells by Macrophages. III. Destruction of Fish Cells by Murine Macrophages, *Dev Comp Immunol.*, 1982 Summer;6(3): 569-578.

Gan, S., et al., Making Sense of Senescence. Molecular Genetic Regulation and Manipulation of Leaf Senescence, *Plant Physiol.*, 1997, 113: 313-319.

Hagerman, A.E., et al., Specificity of Proanthocyanidin-Protein Interactions, *Journal of Biological Chemistry*, 1981, 256(9): 4494-4497.

Hagerman, A.E., et al., Specificity of Tannin-Binding Salivary Proteins Relative to Diet Selection by Mammals, *Canadian Journal of Zoology*, 1992, 71: 628-633.

Halwani, M., et al., Bactericidal Efficacy of Liposomal Aminoglycosides against *Burkholderia cenocepacia*, *Journal of Antimicrobial Chemotherapy*, 2007, 60, 760-769.

Jiménez, A., et al., Evidence for the Presence of the Ascorbate-Glutathione Cycle in Mitochondria and Peroxisomes of Pea Leaves, *Plant Physiol.*, 1997, 114(1): 275-284.

Jiménez, A., et al., Ascorbate-Glutathione Cycle in Mitochondria and Peroxisomes of Pea Leaves: Changes Induced by Leaf Senescence, *Phyton*, 1997, 37:101-108.

Kolodziej, H., et al., Antileishmanial Activity and Immune and Modulatory Effects of Tannins Related Compounds on Leishmania Parasitised RAW 264.7 Cells, *Phytochemistry*, 2005, 66(17): 2056-2071.

Kuboe, et al., Quinone cross-Linked Polysaccharide Hybrid Fiber, *Biomacromolecules*, 2004, 5(2): 348-357.

Lagrimini, L.M., Wound-Induced Deposition of Polyphenols in Transgenic Plants Overexpressing Peroxidase, *Plant Physiol*, 1991, 96: 577-583.

Lamb, C., et al., The Oxidative Burst in Plant disease Resistance, *Annu. Rev. Plant. Physiol. Mol. Bio.*, 1997, 48: 251-275.

Landolt, R., et al., Glyoxysome-like Microbodies in Senescent Spinach Leaves, *Plant Sci.*, 1990, 72(2): 159-163.

Lane, B.G., Oxalate Oxidases and Differentiating Surface Structure in Wheat: Germins, *Biochem J.*, 2000, 349: 309-321.

Leshem, Y.Y., Plant Senescence Processes and Free Radicals, *Free Radical Biol. Med.*, 1988, 5(1): 39-49.

Li, J., et al., Hydrogen Peroxide and Ferulic Acid-Mediated Oxidative Cross-linking of Casein catalyzed by Horseradish Peroxidase and the Impacts on Emulsifying Property and Microstructure of Acidified Gel, *African Journal of Biotechnology*, 2009, 8(24): 6993-6999.

Lin, C.C., et al., Cell Wall Peroxidase Activity, Hydrogen Peroxide Level and NaCl-inhibited Root Growth of Rice Seedlings, *Plant and Soil*, 2001, 230:135-143.

López-Huertas, E., et al., Superoxide Generation in Plant Peroxisomal Membranes: Characterization of Redox Proteins Involved, *Biochem. Soc. Trans.*, 1996, 24: 195S.

López-Huertas, E., et al., Superoxide Radical Generation in Peroxisomal Membranes: Evidence for the Participation of the 18-kDa Integral Membrane Polypeptide, *Free Radical Res.*, 1997, 26(6): 497-506.

Lopez-Huertas, E., et al., Stress Induces Peroxisome Biogenesis Genes, *The EMBO Journal*, 2000, 19(24): 6770-6777.

Low, P.S., et al., The Oxidative Burst in Plant Defense: Function and Signal Transduction, *Physiolooia Plantarum*, 1996, 96(3): 533-542.

Lu, L., et al., Tannin Inhibits HIV_1 Entry by Targeting gp41, *Acta Pharmacol. Sin.*, Feb. 2004, 25(2): 213-218.

Luster, D.G., et al., Orientation of Electron Transport Activities in the Membrane of Intact Glyoxysomes Isolated from Castor Bean Endosperm, *Plant Physiol.*, 1987, 85: 796-800.

Matile, P., et al., Chlorophyll Breakdown in Senescent Leaves, *Plant Physiol.*, 1996, 112(4): 1403-1409.

Mohammadi, M., et al., Changes in Peroxidase and Polyphenol activity in Susceptible and Resistant Wheat Heads Inoculated with fusarium Granminearum and Induced Resistance, *Plant Science*, 2002, 162: 491-498.

Mole, S., et al., In G.R. Waller, Allelochemicals: Role in Agriculture and Forestry, 1987, pp. 572-587, Washington D.C., A.C.S.

Mugabe, C., et al., Mechanism of Enhanced Actibivity of Lipsome-entrapped Aminoglycosides Against Resistant Strains of *Pseudomonas aeruginosa*, *Antimicrob. Agents Chemother.*, 2006, 50: 2016-2022.

Narayanan, B., et al., p53/p21 (WAF1/CIP1) Expression and Its Possible Role in G1 Arrest and Apoptosis in Ellagic Acid Treated Cancer Cells, *Cancer Letters*, 1999, 136: 215-221.

Nishimura, M., et al., Leaf peroxisomes are Directly Transformed to Glyoxysomes During Senescence of Pumpkin Cotyledons, *Protoplasma*, 1993, 175(3-4): 131-137.

Nonaka, G-I., et al., Anti-AIDS Agents, 2: Inhibitory Effects of Tannins on HIV Reverse Transcriptase and HIV Replication in H9 Lymphocyte Cells, *J. Natl. Prod.*, 1990, 53(3): 587-595.

Orozco-Cardenas, M., et al., Hydrogen Peroxide is Generated Systematically in Plant Leaves by Wounding and Systemin via the Octadecanoid Pathway, *Proc. Natl. Acad. Sci. USA*, May 1999, 96: 6553-6557.

Pastori, G.M., et al., An Activated-Oxygen-Mediated Role for Peroxisomes in the Mechanism of Senescence of Pea Leaves, *Planta*, 1994, 193(3): 385-391.

Pastori, G.M., et al., Activated oxygen species and superoxide dismutase activity in peroxisomes from senescent pea leaves, *Proc. R. Soc. Edinb. Sect. B. Biol.*, 1994, 102B: 505-509.

Pastori, G.M., et al., Natural Senescence of Pea Leaves: an Activated Oxygen-Mediated Function for Peroxisomes, *Plant Physiol.*, 1997, 113(2): 411-418.

Pistelli, L., et al., Glyoxylate cycle enzyme activities are induced in senescent pumpkin fruits. *Plant Sci.*, 1996, 119(1-2): 23-29.

Pryor, M.G.M., On the Hrdening of the Ootheca of Blatta Orientalis, *Soc. Lond. Ser. B.*, 1940, 128: 378-393.

(56) References Cited

OTHER PUBLICATIONS

Quideau, S., et al., Main Structural and Stereochemical Aspects of the Antiherpetic Activity of Nonahydroxyterphenoyl-Containing C-Glycosidic Ellagitannins, *Chemistry and Biodiversity*, 2004, 1(2): 247-258.
Ray, H., et al., Transformation of Potato with Cucumber Peroxidase: Expression and disease Response, *Physiological and Molecular Plant Pathology*, 1998, 53: 93-103.
Robertson, J.A., et al., Peroxidase-Mediated Oxidative Cross-Linking and Its Potential to Modify Mechanical Properties in Water-Soluble Polysaccharide Extracts and Cereal grain Residues, Abstract, *J. Agric. Food Chem.*, 2008, 56(5), 1 pg.
Smart, C.M., Gene Expression During Leaf Senescence, *New Phytol.*, 1994, 126(3): 419-448.
Stachowicz, J.J., et al., Reducing Predation Through Chemically Mediated Camouflage: Indirect Effects of Plant Defenses on Herbivores, *Ecology*, 1999, 80(2): 495-509.
Sugumaran, M., Comparative Biochemistry of Eumelanogenesis and the Protective Phenoloidase and Melamin in Insects, *Pigment Cell Res.*, 2002, 15(1): 2-9.
Tanimura, S., et al., Suppression of Tumor Cell Invasiveness by Hydrolyzable Tannins (Plant Polyphenols) via the Inhibition of Matrix Metalloproteinase-2/-9 Activity, *Biochemical and Biophysical Research Communications*, 2005, 330: 1306-1313.
Thompson, J.E., et al., Tansley Review No. 8. The Role of Free Radicals in Senescence and Wounding, *New Phytol.*, 1987, 105: 317-344.
Van Den Bosch, H., et al., Biochemistry of Peroxisomes, *Annu. Rev. Biochem.*, 1992, 61: 157-197.
Van Gerlder, C.W.G., et al., Sequence and Structural Features of Plant and Fungal Tyrosinases, *Phytochemistry*, 1997, 45(7): 1309-1323.
Wang, S.X., et al., A crosslinked Cofactor in Lysyl Oxidase: Redox Function for Amino Acid Side Chains, *Science*, 1996, 273(5278): 1078-1084.
Weiss, et al., Review: Conjugated Linoleic Acid: Historical Context and Implications 1, *Professional Animal scientist*, Apr. 2004, 20(2): 9 pages.
Willekens, H., et al., Catalase is a Sink for $H_2O_2$ and is Indispensable for Streee Defence in $C_3$ Plants, *The EMBO Journal*, 1997, 16(16): 4806-4816.
Woo, E.-J., et al., Germin is a Manganese Containing Homohexamer with Oxalate Oxidase and Superoxide Dismutase Activities, *Nature Structural Biology*, 2000, 7(11): 1036-1040.
Yamaguchi, K., et al., A Novel Isoenzyme of Ascorbate Peroxidase Localized on Glyoxysomal and Leaf Peroxisomal Membranes in Pumpkin, *Plant Cell Physiol.*, 1995, 36(6): 1157-1162.
Yamamoto, T., et al., Roles of Catalase and Hydrogen peroxide in Green Tea Polyphenol-Induced Chemopreventive Effects, *Journal of Pharmacology and Experimental Therapeutics Fast forward*, 2003, 32 Pages, DOI:10.1124/jpet.103.058891, JPET #58891.
Yang, L-L., et al., Induction of Apoptosis by Hydrolyzable Tannins from Eugenia Jambos L. on Human Leukemia Cells, *Cancer Letters*, 2000, 157:65-75.
Zheng, C.J., et al., Fatty Acid Synthesis is a Target for Antibacterial Activity of Unsaturated Fatty Acids, *FEBS Letters*, 2005, 579: 5157-5162.
U.S. Appl. No. 12/868,634, filed Mar. 1, 2010, Huang,et al.
U.S. Appl. No. 12/715,270, filed Mar. 1, 2010, Huang,et al.
U.S. Appl. No. 13/135,124, filed Jun. 24, 2011, Huang,et al.
U.S. Appl. No. 13/135,125, filed Jun. 24, 2011, Huang,et al.
U.S. Appl. No. 13/135,128, filed Jun. 24, 2011, Huang,et al.
U.S. Appl. No. 13/135,123, filed Jun. 24, 2011, Huang,et al.
Glossary of Medical Education Terms. (Online) URL: http://www.iime.org/glossary.htm [retrived on Mar. 24, 2011].
Mattiello, T. et al. Effects of Pomegranate juice and extract polyphenols on platelet function. J med food 12(2): (2009).
Palombo, E. A. Phytochemicals from traditional medicinal plants used in the treatment of diarrhea: Modes of action and effects on intrstinal function. Pyhtotherapy research 20: 717-724 (2006).
Youn H. J. et al. Screening of the anticoccidial effects of herb extracts against *Eimeria tenella*. Veterinary parasitology 96: 257-263 (2001).
International Search Report for PCT/US2010/025805, Apr. 23, 2010, Metaactiv, Inc.—related case.
International Search Report for PCT/US2012/043900, Jan. 30, 2013, LiveLeaf, Inc.—related case.
Absolute Astronomy, Catechin, The Source of this article is Wikipedia,http://en.wikipedia.org/w/index.php?title=Catechin &oldid=77274034, Jan. 2008, 5 pages.
Agnivesa, Caraka Samhita, Edited & translated by P.V. Sharma, vol. II: Chaukhamba Orientelia, Varanasi, Edn. $5^{th}$, 2000. [time of origin 1000 BC-$4^{th}$ century] p. 418.
Akagawa et al., Production of Hydrogen Peroxide by Polyphenols and Polyphenol-rich Beverages UndeQuasi-physiological Conditions, Bioscience Biotechnol Biochem, 67(12), Sep. 2003, pp. 2632-2640.
Akiyama et al. Antibacterial Action of Several Tannins Against *Staphylococcus aureus*, Journal of Antimicrobial Chemotherapy, Jan. 2001, 48, pp. 487-491.
Aoshima et al., Antioxidative and Anti-hydrogen Peroxide Activities of Various Herbal Teas, Department of Chemistry, Faculty of Science, Yamaguchi University, 1677-1 Yoshida, Yamaguchi 753-8512, Japan, Available online Oct. 2, 2006, 1 page.
Bhavamisra; Bhavaprakasa, Edited & translated by Brahmasankara Misra, Part II: Chaukhamba Sanskrit Sansthan, Varanasi, Edn $7^{th}$, 2000. [Time of orgin $16^{th}$ centutey] p. 474.
Bittner, When Quinones Meet Amino Acids: Chemical, Physical, and Biological Consequences, Amino Acids, Apr. 13, 2006, 30, pp. 205-224.
Blair, T.S., Botanic Drugs Their Materia Medica, Pharmacology and Therapeutics, The Therapeutic Digest Publishing Company, Cincnnati, Ohio, Jan. 1917, 20 pages.
Cheng, et al., Progress in Studies on the Antimutagenicity and Anticarcinogenicity of Green Tea Epicatechins, abstract, Chin. Med. Sci. J., Dec. 1991, 6(4), 1 page.
Daff et al, Recent Advances in Polyphenol Research, 2008, Blackwell Publishing, p. 264 (3 pages).
Dayan et al., Oleic Acid-induced Skin Penetration Effects of a Lamellar Delivery System, excerpt (Cosmetics & Toiletries Magazine. Cosmetics And Toiletries.com, http://www.cosmeticsandtoiletries.com/formulating/ingredientIdelivery/9496857.html, Aug. 31, 2007, 2pages.
Definition of "Compound" and "Composition", Grant and Hackh's Chemical Dictionary, $5^{th}$ Ed. McGraw Hill, 1987, 2 pages.
Del Rio, D., et al., HPLC-$MS^n$ Analysis of Phenolic Compounds and Purine Alkaloids in Green and Black Tea, J Agric Food Chem, 2004, 52, pp. 2807-2815.
Dudley et al., Cysteine as an Inhibitor of Polyphenol Oxidase, abstract, Journal of Food Biochemistry. Feb. 23, 2007,13(1), 1 page.
Feldman et al,. Binding Affinities of Gallotannin Analogs with Bovine Serum Albumin: Ramifications for Polyphenol-protein Molecular Recognition, Phytochemistry Jan. 1999, 51, Elsevier Science Ltd., pp. 867-872.
Gallochem Co., Ltd., Gallotannin, http://www.gallochem.com/Gallochem I.htm, Jan. 2002, 4 pages.
Goel et al., Xylanolytic Activity of Ruminal *Streptococcus bovis* in Presence of Tannic Acid, Annals of Microbiology, Jan. 2005, 55(4), pp. 295-297.
Grabber, Mechanical Maceration Divergently Shifts Protein Degradability in Condensed-Tannin vso-Quinone Containing Conserved Forages, Crop Science, Mar. 19, 2008, 48, 2 pages.
Greentealovers.com, Green Tea, White Tea: Health Catechin,http://greentealovers.com/greenteahealthcatechin.htm#catechin, Accessed Feb. 9, 2010, pp. 1-13.
Guo et al., Studies on Protective Mechanisms of Four Components of Green Tea Polyphenols Against Lipid Peroxidation in Synaptosomes, abstract, Biochim. Biophys. Acta Dec. 13, 1996, 1304(3), 1 page.
Guo, et al., Evaluation of Antioxidant Activity and Preventing DNA Damage Effect of Pomegrante Extracts by Chemiluminescence Method, J Agric Food Chem, 2007, 55, pp. 3134-3140.
Hagerman, Tannin Chemistry, Oxford, OH, Jan. 1998, 116 pages.

(56) References Cited

OTHER PUBLICATIONS

Hasson, et al., Protein Cross-linking by Peroxidase: Possible Mechanism for Sclerotization of Insect Cuticle, abstract Archives of Insect Biochemistry and Physiology, Dec. 16, 1986, 1 page.

Heber, Multitargeted therapy of cancer by ellagitannins, 2008, Cancer Letters, 269,pp. 262-268.

Ho, et al., Antioxidative Effect of Polyphenol Extract Prepared from Various Chinese Teas, abstract Prev. Med .Jul. 1992, 21(4), 1 page.

Ishiguro et al., Effects of Conjugated Linoleic Acid on Anaphylaxis and Allergic Pruritus,Biol. Pharm. Bull., Dec. 2002, 25(12), pp. 1655-1657.

Ishikawa et al Effect of Tea Flavonoid Supplementatation on the Susceptibility of Low-density Lipoprotein to Oxidative Modification, abstract, Am J Clin Nutr, Aug. 1997, 66(2), 1 page.

Kabara, J.J., et al., Fatty Acids and Derivatives as Antimicrobial Agents, Antimicrobial Agents and Chemotherapy, 2(1), Jul. 1972, pp. 23-28.

Kamin et al., Stimulation by Dinitrophenol of Formation of Melanin-like Substance from Tyrosine by Rat Liver Homogenates, The Journal of Biological Chemistry, downloaded from www.jbc.org, on Oct. 31, 2008, pp. 735-744.

Kashiwada et al., Antitumor Agents, 129. Tannins and Related Compounds as Selective Cytotoxic Agents, abstract, J Nat Prod, Aug. 1992, 55(8), 1 page.

Kilic et al., Fatty Acid Compositions of Seed Oils of Three Turkish Salvia Species and Biological Activities, Chemistry of Natural Compounds, 41(3), Jan. 2005, Springer Science+Business Media, Inc., pp. 276-279.

Kim et al., Effect of Glutathione, Catechin and Epicatechin on the Survival of *Drosophilia melanogaster* Under Paraquat Treatment, abstract, Biosci. Biotechnol Biochem, Feb. 1997,61(2), 1 page.

Kim et al., Research Note: Antimicrobial Effect of Water-Soluble Muscadine Seed Extracts on *Escherichia coli* 0157:H7, abstract, Journal of Food Protection, 71(7), Jul. 2008, 1 page.

Kim et al., Measurement of Superoxide Dismutase-like Activity of Natural Antioxidants, abstract, Viosci Biotechnol Biochem, May 1995, 59(5), 1 page.

Kahn, Khazaain-al-advia, vol. II (20th century AD), Nadeem Yunas Printer/Sheikh Mohd Basheer & Sons, Lahore, 1911 p. 611.

Krab-Husken, L., Production of Catechols, Microbiology and Technology, Thesis Wageningen University, The Netherlands, Jan. 2002, ISBN 90-5808-678-X, pp. 9-144.

Labieniec, M., et al., Study of Interactions Between Phenolic Compounds and $H_2O_2$ or Cu(II) Ions in B14 Chinese Hamster Cells, Cell Biology Int'l, 2006, 30, pp. 761-768.

Lagrimini, L.M., Wound-Induced Deposition of Polyphenols in Transgenic Plants Overexpressing Peroxidase, Plant Physiol, 1991, 96, pp. 577-583.

Lee et al., Antimicrobial Synergistic Effect of Linolenic Acid and Monoglyceride Against *Bacillus cereus* and *Staphylococcus* Journal of Agricultural and Food Chemistry, Jan. 2002, 50, pp. 2193-2199.

Li, W-Z., et al., Stabilizing the Bactericidal Activity of Hydrogen Peroxide: A Brandnew Function of Certain Chinese Herbs, Chin J Integr Med, Dec. 3, 2012, 6 pages.

Lin, et al Tannin inhibitas HIV-1 entry by targeting gp41 Acta Pharmacol Sin. Feb. 2004: 25(2): 213-218.

Lotito et al., Catechins Delay Lipid Oxidation and α-Tocopherol and β-Carotene Depletion Following Ascorbate Depletion in Human Plasma, Society for Experimental Biology and Medicine, Apr. 2000, pp. 32-38.

MacPhillamy, HB., Drugs from Plants, Plant Science Bulletin, Apr. 1963, 9(2), pp. 1-15.

Matile, P., et al., Chlorophyll Breakdown in Senescent Leaves, Plant Physiol., 1996, 112(4), pp. 1403-1409.

Matsumoto et al. Inhibitory Effects of Tea Catechins, Black Tea Extract and Oolong Tea Extract on Hepatocarcinogenesis in Rat, abstract, Jpn. J. Cancer Res., Oct. 1996, 87(10), 1 page.

Mohammad.Bin Zakariyya Al-Razi; Kitaab-al-Haawi-fil-Tibb, vol. IX (9th century A.D.), Dayerah-al-Ma'aarif Usmania, Hyderabad, (First Edition) 1960 p. 194.

Mohammad.Bin Zakariyya Al-Razi; Kitaab-al-Haawi-fil-Tibb, vol. XX (9th century A.D.), Dayerah-al-Ma'aarif Usmania, Hyderabad, (First Edition) 1967 p. 226.

Morris et al.Affinity Precipitation of Proteins by Polyligands, http://www.ncbi.nlm.nih.gov/pubmed/18601281. Biotechnol Bioeng, Apr. 25, 1993, 41(10), 1 page.

Nanjo et al., Scavenging Effects of Tea Catechins and Their Driviatives on 1, 1-diphenyl-2-picrythydrazyl Radical, abstract free Radic. Bioi. Med .Jan. 1996, 21(6), 1page.

Obermeier et al., Effects of Bioflavonoids on Hepatic P450 Activities, abstract, Xenobiotica, Jun. 1995, 25(6), 1 page.

Omega-3 Fatty Acids, University of Maryland Medical Center, http://www.umm.edulaltmedlarticles/omeza-3-000316.htm accessed Feb. 12, 2010.

Poyrazoglu, E., et al., Organic Acids and Phenolic Compounds in Pomegranates (*Punica granatum* L.) Grown in Turkey, J Food Comp Analysis, 2002, 15, pp. 567-575.

Preuss, H.G., et al., Minimum Inhibitory Concentrations of Herbal Essential Oils and Monolaurin for Gram-positive and Gram-negative Bacteria, Molecular and Cellular Biochemistry, Jan. 2005, 272, pp. 29-34.

Prottey et al., The Mode of Action of Ethyt Lactate as a Treatment for Acne, British Journal of Dermatology, 110(4), Jul. 29, 2006.

Raskin, et al., Can an Apple a Day Keep the Doctor Away?, Current Pharmaceutical Design, 2004, 10, pp. 3419-3429.

Ratnakara, Complied by Naginadasa Chaganalala Saha, Translated by Gopinath Gupta, vol. V: B. Jain Publishers, New Delhi, Edn. 2nd Reprint, Aug. 1999.[This book contains back references from 1000 B.C. to 20 th century] p. 736.

Roginsky et al., Oxidation of Tea Extracts and Tea Catechins by Molecular Oxygen, abstract, Journal of Agricultural Food Chemistry, 52(II), Apr. 30, 2005, 1 page.

Rucker et al, Copper, Lysyl Oxidase, and Extracellular Matrix Protein Cross-linking, The American Journal of Clinical Nutrition, '67(suppl.), Jan. 1998, pp. 996S-1002S.

Sachinidis et al., Are Catechins Natural Tyrosine Kinase Inhibitors? Drug News & Perspectives, Jan. 2002, 15(7), 432, ISSN 0214-0934, 1 page.

Schweikert et al., Scission of Polisaccharides by Peroxidase-Generated Hydroxyl Radicals, Phytochemistry, 53(5), Mar. 1, 2000, 2 pages.

Scott, et al., Evaluation of the Antioxidant Actions of Ferulic Acid and Catechins, abstract, Free Radic Res Commun, Jan. 1993, 19(4), 1 page.

Sebedio, J-L, et al., Vegetable Oil Products, Advances in Conjugated Linoleic Acid Research, Jan. 2003, 2, Urbana, IL, 2 pages.

Selinheimo,Tyrosinase and Laccase as Novel Crosslinking Tools for Food Biopolymers,http:/lib.tkk.fi/Diss/2008/isbn9789513871185/index.html, age last updated: Feb. 2, 2010, Page maintained by: diss@tkk, fi, 5 pages.

Smkaradajisastripade: Aryabhisaka- Gujarati Edited (Hindustana No Vaidyaraja) Translation by Harikrishna Bhagwan Lal Vyas: Sastu Sahitya Vardhaka Karyalaya, Bhadra, Ahmedabad, Edn. 12th, 1957 p. 92.

Stapleton et al., Potentiation of Catechin Gallate-Mediated Sensitization of *Staphylococcus aureus* to Oxacillin by Nongalloylated Catechins, Antimicrobial Agents and Chemotherapy, Feb. 2006, pp. 752-755.

Stark, D., et al., Irritable Bowel Syndrome: A Review of the Role of Intestinal Protozoa and the Importance of their Dectection and Diagnosis, Intl J Parasitology, 2007, 37, pp. 11-20.

Steele, et al., Chemopreventive Efficacy of Black and Green Tea Extracts in Vitro Assays, meeting abstract, Proc Annu Meet Am Assoc Cancer Res, Jan. 1996, 37, 1 page.

Terao et al., Protective Effect of Epicatechin, Epicatechin Gallate, and Quercetin on Lipid Peroxidation in Phospholipid Bilayers, abstract; Arch Biochem Biophys, Jan. 1994, 308(1), 1 page.

Uyama et al., Enzymatic Synthesis and Properties of Polymers from Polyphenols, Advances in Polymer Science, Jan. 2006, 194, ISSN 0065-3195, 1 page.

Valcic et al., Inhibitory Effect of Six Green Tea Catechins and Caffeine on the Growth of Four Selected Human Tumor Cell Lines, abstract, Anticancer Drugs, Jun. 1996, 7(4),1 page.

(56) References Cited

OTHER PUBLICATIONS

Vangasena, Commentator Shaligram Vaisya, Edited Shankar Lalji Jain:Khemraj Shrikrishna Das Prakashan, Bombay, Edn. 1996 p. 1046.

Varghese et al., Effect of Asoka on the Intracellular Glutathione Levels and Skin Tumor Promotion in Mice, abstract, Cancer Lett, Apr. 15, 1993, 69(1), 1 page.

Vermerris, W., et al., Phenolic Compound Biochemistry, Springer, 2008, 13 pages.

Wikipedia, Tannin, http://en.wikipedia.org/wikilTannin, This page was last modified on Jan. 30, 2010, 35 pages.

Wu-Yuan et al.,Gallotannins Inhibit Growth, Water-insoluble Glucan Synthesis, and Aggregation of *Mutans streptococci*, J Dent Res, Jan. 1988, 67(1), pp. 51-55.

Yokozawa, T., et al., Effects of Rhubarb Tannins on Renal Function in Rats with Renal Failure, abstract, Nippon Jinzo Gakkai Shi, Jan. 1993, 35(1), 1 page.

Yoshino et al., Antioxidative Effects of Black Tea Theaflavins and Thearubigin on Lipid Peroxidation of Rat Liver Homogenates Induced by Tert-butyl Hydroperoxide, abstract, Biol Pharm Bull, Jan. 1994, 17(1), 1 page.

Ziya Al-Din Abdullah Ibn Al-Baitar: Ai-Jaam'e—li-Mufradaat-al—Advica-wal—Aghzia, vol. 1 (13$^{th}$ century AD), Matba Amra, Cairo, Egypt, 1874 A.D. p. 162.

Zhang et al., Inhibitory Effects of Jasmine Green Tea epicatechin Isomers on Free Radical-induced Lysis of Red Blood Cells, abstract Life Sci, Jan. 1997, 61(4), 1 page.

Zhu et al., Antioxidant Chemistry of Green Tea Catechins: Oxidation Products of (−)-Epigallocatechin Gallate and (−)-With Peroxidase, Wiley InterScience Journals: Journal of Food Lipids, May 5, 2007, 7(4), 1 page.

Morris et al., "Affinity Precipitation of Proteins by Polyligands",http://www.ncbi.nlm.nih.gov/pubmed/18601281, Biotechnol Bioeng, vol. 41 Issue: 10, 1 pg., Apr. 25, 1993.

Akiyama et al., "Antibacterial Action of Several Tannins Against *Staphylococcus aureus*" *Journal of Antimicrobial Chemotherapy* vol. 48, pp. 487-491, Jan. 2001.

Lee et al., "Antimicrobial Synergistic Effect of Linolenic Acid and Monoglyceride Against *Bacillus cereus* and *Staphylococcus*" *Journal of Agricultural and Food Chemistry*, vol. 50, pp. 2193-2199, Jan. 2002.

Zhu et al., "Antioxidant Chemistry of Green Tea Catechins: Oxidation Products of (−)-Epigallocatechin Gallate and (−)-With Peroxidase", Wiley InterScience:: Journals ::*Journal of Food Lipids*, vol. 7, Issue: 4, 1 Page, Published: May 5, 2007.

Aoshima et al., "Antioxidative and Anti-hydrogen Peroxide Activities of Various Herbal Teas,"Department of Chemistry, Faculty of Science, Yamaguchi University, 1677-1 Yoshida, Yamaguchi 753-8512, Japan, Available online Oct. 24, 2006, 1pg.

Sachinidis et al., Are Catechins Natural Tyrosine Kinase Inhibitors?*Drug News & Perspectives*, Jan. 2002, 15(7): 432, ISSN 0214-0934, 1pg.

Feldman et al. "Binding Affinities of Gallotannin Analogs with Bovine Serum Albumin: Ramifications for Polyphenol-protein Molecular Recognition,"Jan. 1999, *Phytochemistry* 51, Elsevier Science Ltd., pp. 867-872.

Blair, Thomas "Botanic Drugs Their Materia Medica, Pharmacology and Therapeutics," The Therapeutic Digest Publishing Company, Cincinnati, Ohio, Jan. 1917, 20 pgs.

Uyama et al., Enzymatic Synthesis and Properties of Polymers from Polyphenols, *Advances in Polymer Science*, vol. 194, Jan. 2006, ISSN 0065-3195, 1 pg.

Absolute Astronomy, "Catechin", The Source of this article is Wikipedia,http://en.wikipedia.org/w/index.php?title=Catechin&oldid=77274034 Jan. 2008, 5 pgs.

Valcic et al."Inhibitory Effect of Six Green Tea Catechins and Caffeine on the Growth of Four Selected Human Tumor Cell Lines," abstract, *Anticancer Drugs*, Jun. 1996, 7(4),1 pg.

Terao et al., "Protective Effect of Epicatechin, Epicatechin Gallate, and Quercetin on Lipid Peroxidation in Phospholipid Bilayers,"abstract,*Arch Biochem. Biophys.*, Jan. 1994, 308(1), 1pg.

Guo et al.,"Studies on Protective Mechanisms of Four Components of Green Tea Polyphenols Against Lipid Peroxidation in Synaptosomes,"abstract, *Biochim. Biophys. Acta.*, Dec. 13, 1996, 1304(3), 1pg.

Yoshino et al., "Antioxidative Effects of Black Tea Theaflavins and Thearubigin on Lipid Peroxidation of Rat Liver Homogenates Induced by Tert-butyl Hydroperoxide,"abstract,*Biol. Pharm. Bull.*, Jan. 1994, 17(1), 1 pg.

Kim et al., "Effect of Glutathione, Catechin, and Epicatechin on the Survival of *Drosophilia melanogaster* Under Paraquat Treatment," abstract, *Biosci. Biotechnol Biochem.*, Feb. 1997, 61(2), 1 pg.

Kim et al., "Measurement of Superoxide Dismutase-like Activity of Natural Antioxidants," abstract,*Viosci Biotechnol Biochem.*, May 1995, 59(5), 1 pg.

Varghese et al., "Effect of Asoka on the Intracellular Glutathione Levels and Skin Tumor Promotion in Mice,"abstract,*Cancer Lett.*, Apr. 15, 1993, 69(1), 1 pg.

Cheng et al., "Progress in Studies on the Antimutagenicity and Anticarcinogenicity of Green Tea Epicatechins,"abstract,*Chin. Med. Sci. J.*, Dec. 1991, 6(4), 1 pg.

Scott et al., "Evaluation of the Antioxidant Actions of Ferulic Acid and Catechins," abstract,*Free Radic. Res. Commun.*, Jan. 1993, 19(4), 1 pg.

Matsumoto et al. "Inhibitory Effects of Tea Catechins, Black Tea Extract and Oolong Tea Extract on Hepatocarcinogenesis in Rat," abstract,*Jpn. J. Cancer Res.*, Oct. 1996, 87(10), 1 pg.

Zhang et al., "Inhibitory Effects of Jasmine Green Tea epicatechin Isomers on Free Radical-induced Lysis of Red Blood Cells," abstract,*Life Sci.*, Jan. 1997, 61(4), 1 pg.

Ho et al., "Antioxidative Effect of Polyphenol Extract Prepared from Various Chinese Teas," abstract,*Prev. Med.*, Jul. 1992, 21(4), 1 pg.

Steele et al., "Chemopreventive Efficacy of Black and Green Tea Extracts in Vitro Assays," meeting abstract,*Proc. Annu. Meet. Am. Assoc. Cancer Res.*, Jan. 1996, 37, 1pg.

Ishikawa et al. "Effect of Tea Flavonoid Supplementatation on the Susceptibility of Low-density Lipoprotein to Oxidative Modification," abstract, *Am. J.Clin. Nutr.*, Aug. 1997, 66(2), 1 pg.

Nanjo et al., "Scavenging Effects of Tea Catechins and Their Drivi-atives on 1,1-diphenyl-2-picrythydrazyl Radical," abstract,*Free Radic. Biol. Med.*, Jan. 1996, 21(6), 1pg.

Kashiwada et al., "Antitumor Agents, 129. Tannins and Related Compounds as selective Cytotoxic Agents," abstract,*J. Nat. Prod.*, Aug. 1992, 55(8), 1 pg.

Yokozawa et al., "Effects of Rhubarb Tannins on Renal Function in Rats with Renal Failure," abstract,*Nippon Jinzo Gakkai Shi*, Jan. 1993, 35(1), 1 pg.

Obermeier et al., "Effects of Bioflavonoids on Hepatic P450 Activities," abstract,*Xenobiotica*, 25(6), Jun. 1995, 1 pg.

Lotito et al., "Catechins Delay Lipid Oxidation andα-Tocopherol and β-Carotene Depletion Following Ascorbate Depletion in Human Plasma," Antioxidant Activity of Catechins in Human Plasma, Physical Chemistry—PRALIB, School of Pharmacy and Biochemistry, University of Buenos Aires, 1113-Buenos Aires, Argentina, Society for Experimental Biology and Medicine, Apr. 2000, pp. 32-38.

Rucker et al., Copper Lysyl Oxidase, and Extracellular Matrix Protein Cross-linking,*The American Journal of Clinical Nutrition*, 67 (suppl.), Jan. 1998, pp. 996S-1002S.

Dudley et al., "Cysteine as an Inhibitor of Polyphenol Oxidase,"abstract,*Journal of Food Biochemistry*, vol. 13, Issue 1, Published Online Feb. 23, 2007, 1 pg.

Ishiguro et al., "Effects of Conjugated Linoleic Acid on Anaphylaxis and Allergic Pruritus,"*Biol. Pharm. Bull.*, Dec. 2002, 25(12), pp. 1655-1657.

Parrish, Jr. et al., "Effects of Conjugated Linoleic Acid (CLA) on Swine Performance and Body Composition," Jan. 1998,*1997 Swine Research Report*, Iowa State University, AS-638:187-190.

Kilic et al., "Fatty Acid Compositions of Seed Oils of Three Turkish*Salvia* Species and Biological Activities," *Chemistry of Natural Compounds*, vol. 41, No. 3, Jan. 2005, Springer Science+Business Media, Inc., pp. 276-279.

(56) References Cited

OTHER PUBLICATIONS

Kabara et al., "Fatty Acids and Derivatives as Antimicrobial Agents," *Antimicrobial Agents and Chemotherapy*, vol. 2, No. 1, Jul. 1972, pp. 23-28.

Zheng et al., Fatty Acid Synthesis is a Target for Antibacterial Activity of Unsaturated Fatty Acids, *Federation of European Biochemical Societies Letters*, 579, available online Aug. 26, 2005, pp. 5157-5162.

Gallochem Co.,Ltd., "Gallotannin",http://www.gallochem.com/GallochemI.htm, Jan. 2002, 2 pgs.

Wu-Yuan et al., "Gallotannins Inhibit Growth, Water-insoluble Glucan Synthesis, and Aggregation of *Mutans streptococci*,"*J Dent Res*, 67(1), Jan. 1988, pp. 51-55.

Greentealovers.com, Green Tea, White Tea: Health Catechin,http://greentealovers.com/greenteahealthcatechin.htm#catechin,pp. 1-13, Accessed Feb. 9, 2010.

Yamamoto et al., "Studies on Quinone Cross-linking Adhesion Mechanism and Preparation of Antifouling Surfaces Toward the Blue Mussel,"abstract, *Journal of Marine Bitechnology*, vol. 5, No. 2-3, May 1997. 1 pg.

Grabber, "Mechanical Maceration Divergently Shifts Protein Degradability in Condensed-Tannin v*so*-Quinone Containing Conserved Forages," *Crop Science*, 48, published online Mar. 19, 2008, 2 pgs.

Preuss et al., "Minimum Inhibitory Concentrations of Herbal Essential Oils and Monolaurin for Gram-positive and Gram-negative Bacteria," *Molecular and Cellular Biochemistry*, 272, Jan. 2005, pp. 29-34.

Weichers, "Nutraceuticals and Nanoparticles," *Cosmetics & Toiletries Magazine*, CosmeticsAndToiletries.com, http://www.cosmeticsandtoiletries.com/research/techtransfer/9431641.html, posted Aug. 28, 2007, 4 pgs.

Dayan et al., "Oleic Acid-induced Skin Penetration Effects of a Lamellar Delivery System,"excerpt,*Cosmetics & Toiletries Magazine*, CosmeticsAndToiletries.com, http://www.cosmeticsandtoiletries.com/formulating/ingredient/delivery/9496857.html, posted Aug. 31, 2007, 2 pgs.

"Omega-3 Fatty Acids," University of Maryland Medical Center,http://www.umm.edu/altmed/articles/omega-3-000316.htm,accessed Feb. 12, 2010.

Roginsky et al., "Oxidation of Tea Extracts and Tea Catechins by Molecular Oxygen,"abstract,*Journal of Agricultural Food Chemistry*,52(11), Apr. 30, 2005, 1 pg.

Stapleton et al., "Potentiation of Catechin Gallate-Mediated Sensitization of*Staphylococcus aureus* to Oxacillin by Nongalloylated Catechins," *Antimicrobial Agents and Chemotherapy*, Feb. 2006, pp. 752-755.

Krab-Hüsken Leonie, "Production of Catechols, Microbiology and Technology," Thesis Wageningen University, The Netherlands, Jan. 2002, ISBN 90-5808-678-X, pp. 9-143.

Akagawa et al., "Production of Hydrogen Peroxide by Polyphenols and Polyphenol-rich Beverages UnderQuasi-physiological Conditions," *Bioscience Biotechnol. Biochem.*, 67(12), Sep. 2003, pp. 2632-2640.

Hasson et al., "Protein Cross-linking by Peroxidase: Possible Mechanism for Sclerotization of Insect Cuticle," abstract,*Archives of Insect Biochemistry and Physiology*, Dec. 16, 1986, 1 pg.

Robertson et al., Peroxidase-Mediated Oxidative Cross-Linking and Its Potential to Modify Mechanical Properties in Water-Soluble Polysaccharide Extracts and Cereal Grain Residues, J. Agr. Food Chem 2008 56 (5) 1720-6.

Kim et al., "Research Note: Antimicrobial Effect of Water-Soluble Muscadine Seed Extracts on*Escherichia coli* O157:H7," abstract, *Journal of Food Protection*, vol. 71, issue 7, Jul. 2008, 1 pg.

Paepe et al., "Repair of Acetone- and Sodium Lauryl Sulphate-damaged Human Skin Barrier Function Using Topically Applied Emulsions Containing Barner Lipids," abstract. *Journal of European Academy of Dermatology & Venereology*, 16(6), Nov. 2002, 1 pg.

Weiss et al., "Review: Conjugated Linoleic Acid: Historical Context and Implications1,"*Professional Animal Scientist*, Apr. 2004, 29 pgs.

Yamamoto et al., Roles of Catalase and Hydrogen Peroxide in Green Tea Polyphenol-Induced Chemopreventive Effects,*Journal of Pharmacology and Experimental Therapeutics Fast Forward*, first published on Oct. 20, 2003, 2pgs.

Schweikert et al., "Scission of Polisaccharides by Peroxidase-Generated Hydroxyl Radicals", Phytochemistry, vol. 53, Issue: 5, Mar. 1, 2000, 2 pgs.

Kamin et al., Stimulation by Dinitrophenol of Formation of Melanin-like Substance from Tyrosine by Rat Liver Homogenates,*The Journal of Biological Chemistry*, downloaded from www.jbc.org on Oct. 31, 2008, pp. 735-744.

Wikipedia, "Tannin", http://en.wikipedia.org/wiki/Tannin, This page was last modified on Jan. 30, 2010, 35 pgs.

Hagerman, "Tannin Chemistry", Oxford, OH, Jan. 1998, 116 pgs.

Prottey et al., "The Mode of Action of Ethyl Lactate as a Treatment for Acne", Wiley InterScience :: Journals *British Journal of Dermatology*, vol. 110, Issue: 4, Published: Jul. 29, 2006.

Selinheimo, "Tyrosinase and Laccase as Novel Crosslinking Tool for Food Biopolymers", http://lib.tkk.fi/Diss/2008/isbn9789513871185/index.html, Page last updated: Feb. 2, 2010, Page maintained by diss@tkk.fi., 5 Pgs.

Sebedio et al, "Vegetable Oil Products",*Advances in Conjugated Linoleic Acid Research*, vol. 2, Jan. 2003, Urbana, IL, 2 pgs.

Bittner, "When Quinones Meet Amino Acids: Chemical, Physical, and Biological Consequences", Amino Acids, Published online: Apr. 13, 2006, vol. 30, pp. 205-224.

Goel et al., "Xylanolytic Activity of Ruminal *Streptococcus bovis* in Presence of Tannic Acid", Annals of Microbiology, Jan. 2005, vol. 55 (4), p. 295-297.

U.S. Appl. No. 13/726,180, filed Dec. 23, 2012, Huang,et al.—related case.

U.S. Appl. No. 13/772,264, filed Feb. 20, 2013, Huang,et al.—related case.

U.S. Appl. No. 14/027,228, filed Sep. 15, 2013, Huang,et al.—related case.

U.S. Appl. No. 14/027,235, filed Sep. 15, 2013, Huang,et al.—related case.

International Search Report for PCT/US2011/06276-7, filed Aug. 15, 2013, Metaactiv, Inc.

Clyde E.H., Effects of temperature on catalase activity. Ohio Journal of Sceince. 50(6): 273-277 (Nov. 1950).

Croft, K.D. The chemistry and biological effects of flavonoids and phenolic acids. Annals of the New York Academy of Sciences. 845 435-442. 1998.

Dec, J. et al., use of plant material for the decontamination of water polluted with phenols. Biotechnology and Bioengineering, 44, 1132-1139. (1994).

Do-It-Yourself Health, Editor: R. Somerville, Time Life Books, 2 pages (1997).

Gee, J.M., et al. Polyphenolic compounds: Interactions with the gut and implications for human health. Current medical chemistry. 8, 1245-1255 (2001).

Koloski N.A., et al. The brain-gut pathway in functional gastrointestinal disorders is bidirectional. A 12-year prospective population-based study. Gut 61(9): 1284-1290. (2012).

Labieniec, M., et al. Response of digestive gland cells of freshwater mussel unio tumidus to phenolic compound exposure in vivo. Cell Biology International. 31(7): 683-690 (2007).

Longstreth G., et al. Functional bowel disorders. Gastroenterology 130: 1480-1491. 2006.

Parrish, JR et al., Effects of conjugated linoleic acid (cla) on swine performance and body composition. Jan. 1998/1997 Swine Research Report, Iowa State University, AS-638, 187-190 (1998).

Schiller L.R. Definitions, pathophysiology, and evaluation of chronic diarrhea. Best pract res clin gastroenterol 26(5): 551-562. 2012.

Schopfer, P. et al., Realease of reactive oxgen intermediates (Superoxide radicals, hydrogen peroxide, and hydroxyl radicals) and peroxidase in germinating radish seeds controlled by light, gibberellin, and abscisic acid. Plant Physiology vol. 125, pp. 1591-1602 Apr. 2001.

* cited by examiner

ANTIBACTERIAL HAVING AN EXTRACT OF POMEGRANATE COMBINED WITH HYDROGEN PEROXIDE

RELATED APPLICATION(S)

This Patent Application claims priority under 35 U.S.C. 119(e) of the U.S. Provisional Patent Application Ser. No. 61/009,484, filed Dec. 28, 2007, and titled "PLANT-BASED BIOCIDAL MATERIALS AND SYSTEMS". The U.S. Provisional Patent Application Ser. No. 61/009,484, filed Dec. 28, 2007, and titled "PLANT-BASED BIOCIDAL MATERIALS AND SYSTEMS" is hereby incorporated by reference.

FIELD OF THE INVENTION

This invention relates generally to materials and systems that provide a preservative and/or a medicinal effect. More specifically, this invention relates to anti-bacterial, anti-infective, anti-microbial, anti-fungal and antibiotic materials and systems that utilize material obtained from plants.

BACKGROUND OF THE INVENTION

Consumer products and environmental mandates have created a large demand for natural biocides. There are a number of commercial extracts made of plants, notably essential oils, that provide antimicrobial activity. However, all current natural antimicrobials are limited by some combination of low potency, high cost, toxicity, taste, odor and color of the extracted compounds at their minimum effective concentrations. Synergistic combinations of essential oils have met with some success, but their performance still pales compared to common synthetic biocides. The pharmakinetics of all current commercial antimicrobials is still based on dilution of individual molecules.

Plants have various mechanisms for delivering localized and concentrated immune responses against pathogens. Plants cannot rely on general diffusion of antimicrobial compounds throughout their tissues. Effective protective concentrations would be systemically toxic. When plants are exposed to external stress, an almost universal defense mechanism is the local expression of reactive oxygen species (ROS) that initiate compounds rapid formation of physical barriers as well as mounting direct attack against the invading pathogen. These ROS include hydrogen peroxide ($H_2O_2$), superoxide ($O_2^-$), singlet oxygen ($^1O_2^*$), and hydroxyl radical (.OH).

These radicals damage the cell walls of pathogens on contact or create a hyperoxygenated environment that the cell cannot tolerate. They also can initiate reactions of alkaloids, terpenes, phenolics, peptides or other astringent compounds, to aggressively bind and immobilize amino acids of the plant and pathogens.

The cell walls of bacteria and fungi are protected by peroxidase, catalase, and other enzymes that scavenge ROS. Therefore, an effective oxidative attack on a pathogen requires providing a sufficient concentration of ROS molecules to overwhelm the pathogen's defenses.

The cell walls and membranes of eukaryotic organisms are populated with peroxisomes. Subcellular organelles, which are rich in enzymatic proteins, carry out a wide range of functions including β-oxidation of fatty acids, glyoxylate metabolism, and metabolism of reactive oxygen species. $H_2O_2$ producing enzymes NAD(P)H oxidase, oxalate oxidase, and glucose oxidase, are found on the peroxisomal membrane. Peroxisomes contain antioxidant molecules, such as ascorbate and glutathione, the cell's principal $H_2O_2$ degrading enzyme-catalase, and a battery of antioxidant enzymes, including superoxide dismutase, ascorbate peroxidase, dihydro- and monohydroascorbate reductase, glutathione reductase. These tightly regulate the amount of $H_2O_2$ accumulation in healthy plant tissue. Changes in activities of these enzymes are correlated with many situations in which plants experience stress. Accordingly, peroxisomes have been suggested to play important roles in defense against abiotic and biotic stress in plants. Mitochondria and chloroplasts also use $H_2O_2$ as a transduction medium. Superoxides are also converted in the organelle matrix.

Reactive oxygen species (ROS) can destroy invading microorganisms by denaturing proteins, damaging nucleic acids and causing lipid peroxidation, which breaks down lipids in cell membranes. Both plant cells and pathogens are protected, at least in part, from ROS by enzymatic and non-enzymatic defense mechanisms.

Defense against its endogenous ROS as well as a pathogen ROS attack is believed to be provided by the scavenging properties of antioxidant molecules found in the organelles and the cell membranes. Superoxide dismutases (SODs) catalyze the reduction of superoxide to hydrogen peroxide. Hydrogen peroxide is then decomposed to $H_2O$ by the action of catalases and peroxidases. A certain concentration of $H_2O_2$ also diffuses into the intracellular matrix and is released by lysis or mechanical rupture of cells. Cell disruption causes $H_2O_2$ to come in contact with separately compartmentalized polymers and initiates rapid cross-linking of cellular proteins to form a protective barrier at localized stress sites. The in-vivo anti-bacterial efficacy of antibiotics encapsulated in synthetic liposomes was demonstrated to be four times more effective than the free systemic application (Halwani and Cordeiro, et al., 2001). There is much ongoing research on imparting improved transgenic $H_2O_2$ defenses to commercial crops, genetically modified organisms to produce new antimicrobial compounds, and new botanical sources of antimicrobial extracts. Animal macrophages are another example of specialized immune mechanisms for ROS attack on pathogens. There is a clear advantage to localized defensive response over systemic diffusion of antimicrobial chemistry.

Hydrogen peroxide is a common and effective broad spectrum disinfectant, which is notable for its ideal environmental profile ($H_2O_2$ decomposes into water and oxygen) and low toxicity. It is an ubiquitous multifunctional factor in both plant and animal immune and metabolic processes. Hydrogen peroxide is generally regarded as safe (GRAS) by the USDA for use in processing foods when the concentration is less than 1.1%. $H_2O_2$ that has a concentration of 3% is commonly used for topical and oral disinfectant. Commercially produced $H_2O_2$ is synthetically produced but identical to that produced in cells and has been accepted world-wide for processing nearly every industry. It is an excellent broad spectrum antimicrobial, but it is too indiscriminating and volatile for effective use as a product preservative.

The ability to withstand oxidative attack is generally a function of the organism size. Most pathogens are small and more susceptible to ROS damage than plant and animal cells. Once the pathogen is depleted of ROS degrading molecules, further oxidation can damage the cell membrane, causing cell death. This is a completely different mechanism than the blocking of metabolic transduction sites and other highly specific molecular interactions of antibiotics that are becoming alarmingly less effective as bacteria adapt and become resistant.

The tissue of many succulents has a long history of use in traditional medicine as antimicrobial wound dressings and for other medicinal purposes. Aloes are widely cultivated and processed for a variety of purposes. Several species of cacti are less widely commercialized but equally valued in traditional medicine and as a food source. Plants evolved in harsher environments, such as the dessert succulents, tend to have enhanced capacity to produce hydrogen peroxide in response to biotic and abiotic stresses. Cleanly sliced fresh pieces of cacti and aloe plants are traditionally effective against infection largely due to the $H_2O_2$ expression in the plant tissues in response to its injury. Commercially processed aloe gels generally lose their antimicrobial activity.

U.S. Patent Application No. 2002/0034553 teaches a composition of Aloe vera gel, Irish moss and approximately 3% hydrogen peroxide where the aloe vera primarily forms a gel holding the ingredients together in an ointment or lotion which may be applied directly to a cleansed infected or irritated skin tissue area. The application relies on a conventional bulk concentration (1.5%) of $H_2O_2$ to provide an oxygen-rich environment, and it makes no specific teaching regarding functional interactions of $H_2O_2$ and the enzymatic or other cellular chemistries of the plant fractions.

U.S. Pat. No. 6,436,342 teaches an antimicrobial surface sanitizing composition of hydrogen peroxide, plant derived essential oil, and thickener. However, it does not teach interaction between components.

U.S. Pat. Nos. 5,389,369 and 5,756,090 teach haloperoxidase-based systems for killing microorganisms by contacting the microorganisms, in the presence of a peroxide and chloride or bromide, with a haloperoxidase and an antimicrobial activity enhancing α-amino acid. Although highly effective antimicrobials, the systems cannot generally be considered natural products and the components must be separately stored or packaged in anaerobic containers to prevent haloperoxidase/peroxide interaction and depletion prior to dispensing for use.

U.S. Pat. No. 5,389,369 teaches an improved haloperoxidase-based system for killing bacteria, yeast or sporular microorganisms by contacting the microorganisms, in the presence of a peroxide and chloride or bromide, with a haloperoxidase and an antimicrobial activity enhancing α-amino acid. Although the compositions and methods of U.S. Pat. No. 5,389,369 have been found to be highly effective antimicrobials, the components must be separately stored and maintained in order to prevent haloperoxidase/peroxide interaction and depletion prior to dispensing for use.

The above references describe the application of various oxidative antimicrobials in a free liquid dispersion. Ability of a solution of free soluble biocidal compounds to effectively kill pathogens is determined by the probability of individual molecular interactions with the pathogen. This ability rapidly diminishes with volumetric dilution and consumption of the active solute.

For this reason, application of diffuse free active chemicals in solution is grossly inefficient at killing bacteria and fungi, yet this is predominantly how antimicrobials are formulated into commercial products for topical therapeutics, personal care products, commercial and industrial sanitizers, and sanitation or preservation of food and water. This method demands extraction processes that highly concentrate active chemicals. To obtain adequate microbial suppression, product formulations commonly require higher concentrations of these chemicals that would be toxic to the tissues of plants of origin. There are some examples of encapsulation of essential oils for stabilization of fragrance, and commercially available synthetic liposomes for targeted intravenous drug delivery, but there are no commercial examples of ex-vivo generation of unencapsulated plant material complexes for improved antimicrobial efficiency.

Figure 1:
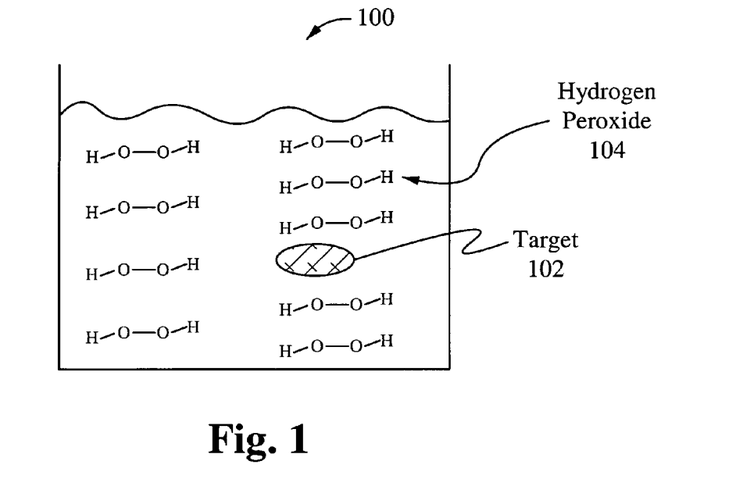

FIG. 1 illustrates a traditional biocidal solution 100. The working principle of traditional biocidal solution is based on free liquid dispersion. The effectiveness of the biocidal compounds solution is determined by the probability of individual molecule that encounters with the pathogen. The target 102 is within the solution 100 which contains free liquid dispersed hydrogen peroxide 104.

Therefore, there exists a need for compositions and methods of preparing microscale antimicrobial complexes or aggregates of stable active chemistries that provide an efficient means of concentrating the assault on pathogenic organisms. Ideally, such antimicrobial complexes should be fast acting with minimal host toxicity and with maximal germicidal action. The compositions should be naturally derived, easy to deliver or formulate, and should not cause damage to host tissue or common surfaces on contact. Depending upon the strength of composition and the time interval of exposure, the compositions should produce antisepsis, disinfection, or sterilization at lower molar concentrations than typical free active chemicals in solution. Such compositions will have utility as an efficient means of controlling microbial population for anti-infection, sterilization, deodorization, sanitation, environmental remediation, preservation of topical products, and safety and preservation of food and water.

SUMMARY OF THE INVENTION

The present invention describes compositions, applications, application methods and methods of producing a biocidal substance with a substrate of biologically reactive material. In some embodiments, the biocidal substance includes plant-tissue aggregates, extracted polymers, or combinations thereof. In some embodiments, the biocidal substance with a substrate of biologically reactive material creates high localized density of bioactive sites for improving microbicidal efficiency and astringent effect.

In one embodiment of the invention, the method of forming and the composition of a plant-based biocidal solution includes a bioactive material and a plant-based substance formed from the cellular material of a plant capable of binding to the bioactive material. In some embodiments, the interaction between the plant-based substance and the bioactive material stabilizes the bioactive material. The combination of the plant-based substance and the bioactive material provides a stable source of providing bioactive material. In some embodiments, the bioactive material is a substrate of compounds of reactive oxygen species. Alternatively, in some embodiments, the bioactive material is hydrogen peroxide. The hydrogen peroxide can be generated endogenously or exogenously. The exogenously added hydrogen peroxide can be obtained directly from commercially available sources. In some embodiments, such hydrogen peroxide has a concentration of 1%-90% hydrogen peroxide in water. Alternatively, the hydrogen peroxide has a concentration of 25%-50% hydrogen peroxide in water. The endogenous generation of hydrogen peroxide can be achieved by measured gross cutting or other physical abiotic stressing of a metabolically viable harvested plant structure or controlled wounding of a pre-harvest plant to activate an expression of an increased $H_2O_2$ acting compound. Alternatively, in some embodiments, the bioactive material is generated by the degradation of added ozone ($O_3$) by an active dismutase in the complex or solution, or in combination with direct addition of the $H_2O_2$.

In some embodiments, the plant-based substance, cellular materials, and plants are obtained naturally or artificially. In some embodiments, the plant-based substance is formed from a cellular fragment, a multivalent polymer, an oligomer, an intact cell, a lignin, a subcellular organelle, a membrane fragment, a soluble protein, a polysaccharide, a phenolic compound, a terpene, an enzyme, and a denatured proteinaceous fragment. In some embodiments, the cellular material comes from a cell of a plant with a hydrogen peroxide acting enzyme on the cell membrane, a membrane bound organelle, or a tissue with the ability to fix and significantly increase the half-life of hydrogen peroxide or other oxygen radical while preserving its bio-reactivity. Most higher plants have some degree of ROS generation and preservation capability in their tissues. In some embodiments, the plant is a species from of the family of Cactaceae, Agavaceae, or Poacea. In some embodiments, the plant is a species with a history of food or medicinal application or Generally Regarded As Safe (GRAS) by the U.S. Department of Agriculture (USDA) or U.S. Food and Drug Administration (FDA). In some embodiments, the plant-based biocidal solution can include water, gas, supercritical fluid, organic solvent, inorganic solvent, or any combination thereof.

In accordance with further embodiments, the bioactive material-degrading enzyme, such as catalase and peroxidase, contained in the cellular material needed to be processed to be at least partially inactivated. This can be accomplished by desiccating, blanching, heating of dried materials, exposing to UV radiation, freeze-thaw cycling, heating or boiling in a solution of water, storing processed or partially processed for natural degradation with time, or exogenously adding of a chemical enzymatic inhibitor.

In some embodiments, the plant-based biocidal material is a natural product. The plant-based biocidal material is able to be used alone, in combination with other oxidizers, material, or in synergistic interaction with additional exogenous or endogenous plant-derived or synthetic antimicrobals. In some further embodiments, the plant-based biocidal material has an effective concentration sufficiently low to dilute a non-functional or undesirable component or characteristic in solution to a sub-functional or sub-concern level.

Another embodiment of the invention is the use of the plant-based biocidal material to impair a target. The use of the plant-based biocidal material is achieved by taking the plant-based substance formed from a cellular material of a plant with a bioactive material and applying the plant-based substance with the bioactive material to a target, such as a pathogen. The applying of the plant-based substance with the bioactive material is able to deliver high localized concentration of the bioactive material to the target. Such application can be for a purpose of providing direct biocidal activity or for biocidal preservation of the formulation. Furthermore, such application can also be applied to a beneficial effect to human or animal wound healing, such as exudate control, wound closure, and rapid scab formation attributable to the aggressive bio-oxidative and protein cross linking capacities of $H_2O_2$ by itself, or in combination with potentiating endogenous and or exogenous co-factors.

Another embodiment of the invention is the method of using the plant-based biocidal material. The use is achieved by taking a plant-based substance formed from a cellular material of a plant with a bioactive material, forming a microscopic cluster, a complex, or an aggregate from a suspension of the plant-based substance, and applying the microscopic cluster, the complex, or the aggregate to a target, such as a pathogen, thereby impairing the target. In some embodiments, the impairment of a target can be oxidative damage. In other embodiments, applying the microscopic cluster, the complex, or the aggregate to impair a target is for the purpose of stable binding of a dense localized concentration of hydrogen peroxide to enact a nearly simultaneous oxidative attack with sufficient number and rate of reactions to overwhelm oxygen scavenging and enzymatic Reactive Oxygen Species (ROS) defenses of pathogens or a combination of isolation, immobilization and ROS attack.

BRIEF DESCRIPTION OF THE DRAWINGS

FIG. 1 illustrates a solution containing free liquid dispersion of hydrogen peroxide taught by prior art.

FIG. 2 illustrates a plant-based biocidal material in accordance with the present invention.

FIG. 3 illustrates a flowchart of a method of combining plant-based substance and a solution containing bioactive material in accordance with the present invention.

FIGS. 4A and 4B illustrate uses of plant-based biocidal solution in accordance with the present invention.

FIG. 5 illustrates another use of plant-based biocidal solution in the form of microscopic clusters, complexes, and aggregates in accordance with the present invention.

DETAILED DESCRIPTION OF THE INVENTION:

The antimicrobial potency of a liquid composition is a function of the local density of $H_2O_2$ or other bio-active molecules within reactive proximity of the pathogen. The biocidal effectiveness of each individual aggregate does not substantially change with gross dilution though the probability of aggregate-pathogen encounter, and therefore the kill rate in time will be an inverse function of gross dilution. In the present invention, the antimicrobial aggregate or plant-based substance has the potential to deliver a high localized concentration that is more efficient at killing organisms than a diffuse dispersion of the same molar concentration of free active molecules. This composition, and method of producing efficient plant-based antimicrobial compositions with extremely low minimum effective concentration is both novel and valuable in a multitude of commercial uses. It will be readily apparent to one skilled in the art that other various modifications can be made, and the present application is not limited to the use of $H_2O_2$ or antimicrobial activity.

One embodiment of the composition in the present invention utilizes aspects of oxidative defenses mechanisms that occur in most plants. Plants generate $H_2O_2$ as a multifunction molecule for both defense and metabolic functions. Plant cellular structures, such as peroxosomes, mitochondria, and cell membranes, are sites of $H_2O_2$ generating and regulating enzymes. $H_2O_2$ related enzymes, such as catalases, peroxidases, oxalate oxidases, glucose oxidases and dismutases, have the ability to capture and catalyse reactions with $H_2O_2$. Even if inactive in their original function, the structure of these molecules can provide low energy binding sites for fixing $H_2O_2$ while preserving its bio-reactivity. Therefore, the present invention uses a plant-based substance formed from the cellular material of a plant to bind various bioactive material, including $H_2O_2$.

Certain active enzymes, such as catalases and peroxidases, decompose $H_2O_2$ and are undesirable in the compositions of the invention. These enzymes are susceptible to degradation; therefore, heat, cold, dessication or time are essential steps used in the process to reduce the population of $H_2O_2$ reducing enzymes prior to the addition of exogenous $H_2O_2$.

The plant-based biocidal solution of the invention can be applied to, but not limited to: cosmetic preservative, food preservative, water sanitizer, persistent surface sanitizer, water preservative, environmental remediation, sewage treatment, medical therapy of wounds, medical treatment of gastric infections, medical treatment of chronic ulcers, medical treatment of gingivitis, treatment of halitosis, sterilization of medical instruments, sterilization of contact lenses, sterilization of surfaces, shelf life extension of fresh foods, reduction of bacteria in aquatic farms or aquaria, prophylactic prevention of gastric infections, first aid antiseptics, and treatment of fungal infections.

Some embodiments of the present invention provide a natural antimicrobial extract that has fewer adverse toxicological and environmental impacts than traditional biocides such as chlorine, phenolics, aldehydes and quaternary ammonium salts.

Alternatively, some embodiments of the invention use only natural plant tissues in combination with only exogenous oxidizers approved by the USDA for food use and GRAS from the following: hydrogen peroxide, ozone. The $H_2O_2$ containing solution is then diluted by at least 100:1 before commercial application. At such dilutions, remaining free $H_2O_2$ or $O_3$ will preferably spontaneously decompose in a short period of time at room temperature, leaving only chemical species consistent with those native in the plant source.

Some embodiments of the invention obtain sufficient antimicrobial potency at very high dilutions to reduce the direct or accumulated effects of undesirable substances that have toxicity or produce taste, odor, or color. This uniquely allows the use of simplified whole plant tissue utilization with reduced or eliminated need for selective extraction or isolation processes. This further improves the ability and opportunities for producing compositions that are natural and potentially organic product or ingredient.

Some embodiments of the invention significantly increase the half life of the bound $H_2O_2$ in its composition as compared to free $H_2O_2$. The antimicrobial activity of the 100 ng/ml solution was challenged at 2, 7, 17, and 30 days, and exhibited no significant reduction in *E. Coli* killing capability. After 90 days at room temperature and ambient flourescent light exposure, the original master batch of Pachycereus pecten-aboriginum composition showed no reduction in potency.

Some embodiments of the invention also provide a composition with non-biocidal benefits in animal and human wound healing. Compositions prepared from the two species of Cactaceae induce rapid closure of cuts, exudate control, and rapid fibrin scab formation on open abrasions.

Some embodiments of the invention provide a biocidal composition with a mechanism of action less prone to resistance selection. Packet oxidative attack that overwhelms pathogen defenses minimizes weakened survivors to propagate resistance. Some embodiments of the invention provide a composition with a significantly lower effective concentration than most synthetic disinfectants and antibiotics. The tested compositions contain less than 10 ng whole dry plant mass/gram of water, and they are 100% effective against a broad spectrum of yeast, gram-positive bacteria, and gram-negative bacteria in vitro. Further, some embodiments of the invention provide increased safety and dosage margins in animal/human medicinal and food applications. Hydrogen peroxide oxidative attack on pathogens is selective against non-eukaryotes and has no accumulative by-products.

The invention provides a composition for topical application on human and animal skin, mucosa and wounds with minimal irritation, sensitization or chemically induced discomfort at the effective concentrations. Hydrogen peroxide defenses and enzymatic mechanisms of plants are largely homologous and therefore compatible with mammilian cell defenses. Very low effective overall concentration dilutes potential sensitizing and irritating components to insignificant levels. The composition is also compatible with standards of wound care such as hydrogen peroxide, benzalkonium chloride, alcohol or saline used in debridement.

Further, some embodiments of the invention provide an antimicrobial composition that can maintain antimicrobial effectiveness at low concentrations in water and high levels of dilution into carriers such as water, alcohol, propylene glycol, oil emulsions, fatty acid emulsions, hydrogels, or plant-derived bulking carriers, such as aloe for antiseptic formulations for injuries to human and animal skin, and mucosa to provide positive benefit during the initial stages of healing. A preferred method of production produces a high biocidal potency water soluble composition without secondary concentrating processes.

Some embodiments of the invention provide a mycocidal composition and an enhanced mycocidal composition with the addition of non-oxidative mycocidal co-ingredients such as essential oils, particularly the essential oils of citron, cinnamon, usnic acid, eucalyptus, oregano, almond, or the formulation with surfactants such as sodium laurel sulfate, or other ionic or non-ionic surfactants. The aggressive oxidative nature of hydrogen peroxide is highly effective against yeasts, such as *Candida-albicans*. Mycocidal effectiveness is limited at the low concentrations against larger eukaryotic cells and fungi with high level of external catalase, such as *Aspergillus niger*. Sub-lethal concentration can maintain mycostasis of *Aspergillus niger*, but co-ingredients as mentioned provide improved killing.

Diluted extracts can be used on surfaces, skin, underclothing, shoes, oral mucosa, or other moist porous environments to control bacteria induced odor. Diluted extract can be administered orally to control gastroenteritis or other bacteria induced gastric disorders in humans and animals. The plant species tested have a substantial history of ingestion for folk remedies. Some embodiments of the invention produce a composition that is effective at sanitizing and preserving potable water without the adverse toxicity, taste, and odor associated with chlorination. The preferred composition of oxidizing molecule complex or aggregates provides a stable, persistent antimicrobial activity at effective dilutions comparable to or lower than free chemical oxidizing disinfectants, such as chlorine.

The use of endogenous or added $H_2O_2$ to crosslink free soluble proteinaceous compounds that have been extracted from plant tissue. $H_2O_2$ plays a key role in the normal lignification of plant cell walls and polymerization of free soluble proteins released when plant cells are damaged or stressed. This is a defensive adaptation in plants that potentially seals a wound or thickens the cell walls for a mechanical barrier to limit loss of liquids and deter pathogen access. The enzymatic reduction of hydrogen peroxide is known to initiate the cross-linking and polymerization of soluble proteins to form dimers, trimers, and higher protein polymers. It is suggested that catalase and peroxidase catalyzes the oxidation of hydrogen donors to form free radicals quinones or other potential intermediates, which subsequently interact with, cross link, and alter the soluble proteins (Stahman et al., Biochem 3. Jul. 1, 2000; 349(Pt 1): 309-321). The harvesting, storage, dessication, mechanical reduction, and extraction processes all cause the loss of endogenous $H_2O_2$. Addition of $H_2O_2$ to the extracted soluble proteins can initiate cross-linking, particularly in the presence of intact peroxidase. The use of fresh, hydrated or partially-dessicated plant tissues can contain a significant level of endogenous $H_2O_2$. Cold processing consisting of macerating tissue and soaking in cool water or cold pressing, and these processes release protein fragments from ruptured and autolyzed cells along with some content of endogenous $H_2O_2$ that can promote formation of cross-linked proteinaceous aggregates or complexes without addition of $H_2O_2$. The use of endogenous $H_2O_2$ does not necessarily eliminate the need for exogenous $H_2O_2$ in composition to saturate the binding sites. The use of synthetic chemicals, except $H_2O_2$, to initiate cross-linking is typically undesirable for natural product applications.

The use of cell wall lysates on intact tissues increases the available free compounds available for subsequent aggregate formation. This can be used to take the place of mechanical pulverization, heating of the solution, or freezing to separate and disrupt cells and extract soluble proteins and enzymes.

Some embodiments of the invention provide a composition that can be produced using a very small amount of raw plant material to allow sustainable and economical manufacture. The present method of production requires less than one milligram of dessicated whole plant mass to produce a kg of antimicrobial solution at final dilution, but those skilled in the art will understand that the composition can be produced and used at higher and lower concentrations. This also facilitates batch blending of unprocessed dry plant stock to reduce variability related to season, age, cultivation, and other factors.

The plant materials preferably used in production of this invention are characterized by high capacity to produce antimicrobial ROS, astringent polymers or the combination as innate microbial defenses. Physical adaptations to environmental stresses are often a good indicator of these.

The outer coverings of seeds and fruits tend to exhibit the ability to withstand exceptional environmental stress in protecting germinating seedlings. Such adaptations are good indicators of the highly developed oxidative stress and pathogen management systems of these plants. A particularly environmentally durable $H_2O_2$-acting oxalate oxidase enzyme is commonly known as germin, a manganese containing homohexamer with both oxalate oxidase and superoxide dismutase activities. It is prevalent in seeds, buds, and sprouts to provide protection during the vulnerable germination phases. Cereal grains are noteworthy for containing a high concentration of germins in roots and seed membranes to protect the seeds and seedlings during germination. The discarded hulls of the seed germs are a potential source of tissue useful with this invention. An example is the cereal grains of the Poaceae family.

Succulent tissues of Aloe, Pachycereus, and Opuntia were selected for their history in folk medicinal use. Their characteristics are consistent with xeric plants with high ROS defensive chemistry content, and are available without environmental, regulatory or cultivation concerns. These succulants have structures adapted to retain a large quantity of water and asexually reproduce through stem/stalk cuttings. Their tissues have rapid lignification ability and high endogenous $H_2O_2$ storage capacity suggesting a high population of peroxisomes and membrane bound ROS management enzymes.

Plant tissues known for high polyphenol content also are good candidates for the plant sources. Examples are the barks and leaves of the Fagoseae and Theaceae families.

Antimicrobial compositions of this invention have been produced from tissues of the plant families: Agavaceae, Cactaceae, Poaceae, Theaceae, Leguminosae, Fagoseae and Lythraceae, However, the present invention is not limited to these families. A person skilled in the art will understand that the polymers, structures and enzymes capable of binding, incorporating, sequestering or reacting with ROS or ROS producing materials, and other proper material are able to be used as embodiments of the present invention. Specific examples of common plant tissues that have been successfully used by the inventors in the production of this composition include: wheat husk, barley germ, rice hull, various columnar cacti, pomegranate husk, green tea leaves, aloe vera leaves, mung beans and carrot. The preferred plants are commercially cultivated species that are generally regarded as safe (GRAS) by the US FDA thus having a history of low toxicity.

Regardless of the antimicrobial mechanism, the suitability and potency of a plant materials is subject to many species dependent, seasonal and cultivation factors. A major advantage of the present invention is the consistent level of potency that can be achieved by sub-saturation of the plant material binding sites. The addition of $H_2O_2$ or other substrate at a molar quantity below the minimum baseline that the plant material can be assured to bind, provides dose control and quality metrics that are rare in natural products.

The method of complexing a large number of bioactive molecules can produce enhanced antimicrobial effectiveness at lower concentrations than equivalent dilution of free active components. An antimicrobial composition is provided that can be an effective plant based biocide at below 10 ppm molar concentration of the bioactive raw ingredient. In the case of hydrogen peroxide as the bioactive component, this results in low native toxicity and minimum accumulation concern levels to facilitate regulatory approvals as a preservative additive for foods, cosmetics, and medicines. Other concentrations may be used as appropriate for the applications. Bacterial inhibition in aqueous solutions has been demonstrated at concentrations as low as 10 parts per billion. The ability to remain biocidally functional at such low concentrations is valuable in uncontrolled dilution situations such as for aquafarms, surface water or ground water remediation, agricultural sanitation, drinking water decontamination and industrial water processing.

Embodiments of the Present Invention:

Embodiments of the present invention are directed to a method of forming and the composition of a plant-based biocidal solution. The plant-based biocidal solution contains a bioactive material and a plant-based complex. In some embodiments, the bioactive material can be an oxidizing substrate capable of releasing reactive oxygen species. Reactive oxygen species (ROS) are ions or very small molecules that include oxygen ions, free radicals, and peroxides, both inorganic and organic. They are highly reactive due to the presence of unpaired electrons. In some embodiments, the bioactive material is hydrogen peroxide. In some embodiments the bioactive material can be, but is not limited to, ozone, fatty acid peroxides, other peroxides, halogens, antibiotics, or other bioactive compounds that can be performance enhanced by stabilization and concentrated by the plant compound complex.

The plant-based complex can be formed from a cellular material of a plant cell, a plant cell fragment or fragments, a single or network of multivalent plant polymer or oligomer, or a combination of cellular fragments and plant polymers or oligomers capable of binding, fixing, sequestering, attracting or incorporating multiple instances of bioactive molecules or radicals in a manner that maintains their bio-reactive function. Binding, fixing or incorporating refers to any chemical bonding including covalent, ionic, Van der Waals, or hydrogen bonds, electrostatic attraction, enzymatic retention, entrapment, entanglement or other mechanism that immobilizes the bioactive component to the plant material. This includes reversible and non-reversible chemical reactions that incorporate the bioactive material, a degradation product a molecular subunit or ROS.

Figure 2:
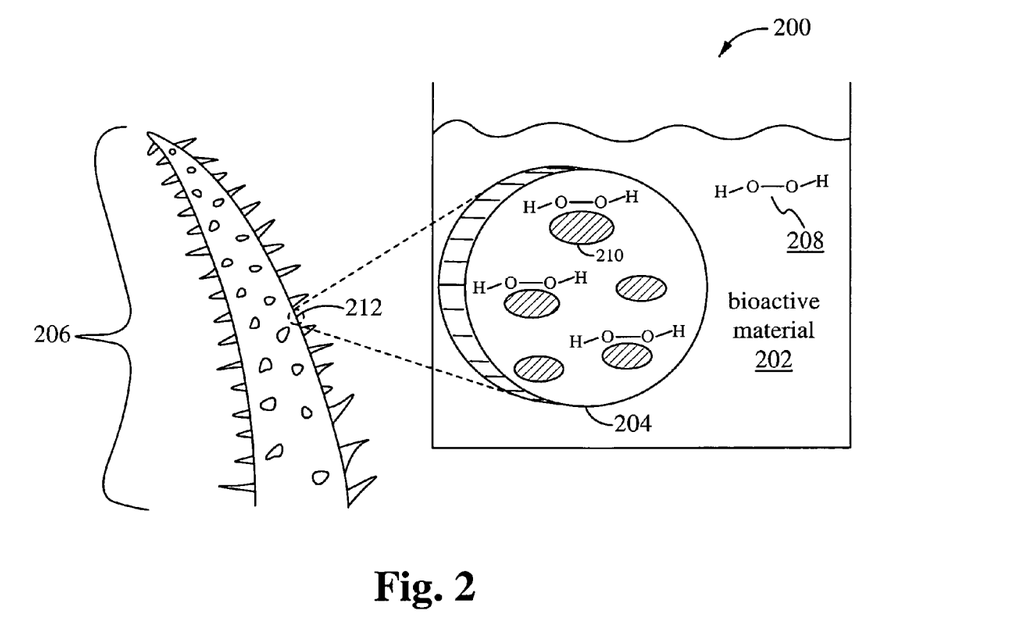

FIG. 2 illustrates a plant-based biocidal solution 200 of the present invention. The plant-based biocidal solution 200 contains a plant-based substance 204. The plant-based substance 204 has cites 210 to bind bioactive material 202, including hydrogen peroxide 208. The plant-based substance 204 can be formed from a cellular material 212 of a plant 206. In some embodiments, the plant-based biocidal solution 200 contains a solvent. The solvent can be water, organic solvent, inorganic solvent, gas, supercritical fluid, or any combination thereof.

In some embodiments, the plant-based complex 204 is formed from the cellular material 212 in the form of any of the following singularly or in combination: (1) cellular fragments with attached molecules with compatible bioactive material binding sites 210, (2) partially or wholly intact plant cellular structures, membrane fragments, invagintions or organelles populated with bioactive material binding capable molecules, (3) proteinaceous aggregates or fibrils of intact, partially denatured or fragmented enzymes, or other proteins with the ability to bind bioactive material in a bio-reactive state, and (4) other soluble compounds that may provide useful independent activity, synergistic activity or act as reaction co-factors: Alternatively, in some embodiments, plant cellular material 212 is peroxosomes, mitochondria and cell membranes, which are sites of $H_2O_2$ generating and regulating enzymes. In some embodiments, the sites 210 are bioactive material related enzymes, such as catalases, peroxidases, oxalate oxidases, glucose oxidases, and dismutases, having the ability to capture and/or catalyze reactions with bioactive material. Even if inactive in their original function, the structure of these molecules can provide low energy binding sites for fixing bioactive material while preserving its bio-reactivity.

In some embodiments, the bioactive material 202 can be a substrate of a molecule or compound that generates reactive oxygen species when triggered by a catalyst, enzyme or other co-factor. Alternatively, the bioactive material 202 can be hydrogen peroxide 208. Some hydrogen peroxide can be obtained from an endogenous source in the plant material. The exogenous addition of hydrogen peroxide can be obtained directly from commercially available sources. In some embodiments, the exogenous commercial hydrogen peroxide 208 has a concentration of 1-100%. In some embodiments, the concentration of hydrogen peroxide is 1-50%. In some embodiments, the hydrogen peroxide concentration is 20-50%. A sufficient concentration is necessary to accommodate the water content of the aggregate solution to allow subsequent dilutions. The concentration must create a sufficiently high diffusion gradient around the plant material to overcome any remaining $H_2O_2$ degrading enzymes.

The concentrated exogenous $H_2O_2$ added to the concentrated aqueous suspension/solution of the plant material provides for an higher diffusion gradient to substantially overcome any diffusion and charge repulsive gradients in the plant material complex to achieve target saturation of the $H_2O_2$ binding sites in an economically efficient production time.

In some embodiments, the endogenous expression or production of endogenous bioactive material 202, binding enzymes or desired multivalent plant molecules can be enhanced by mechanical, abiotic or biotic stress to the metabolically active plant source or tissue. Pathogen attack, environmental stress and mechanical trauma to induce pre-harvest stress and post harvest cutting into metabolically active plant structures stimulate defensive responses that may provide for increased production of desired plant material such as polyphenols, peroxidases or lignin forming precursors.

Alternatively, in some embodiments, the bioactive material 202 can also be generated by the treatment of the plant material solution with ozone ($O_3$). Ozone can be used alone or in combination with exogenous $H_2O_2$. Direct aeration of the plant material solution with $O_3$ from a commercial source or a electrical Ozone generator dissolves into the solution for incorporation. Dismutases in the composition enzymatically convert $H_2O$ and $O_3$ into $H_2O_2$ and $O_2$. This method can be more difficult to control, but it is desirable in circumstances where concentrated $H_2O_2$ is not available.

In another alternative embodiment, the plant material can be combined as a kit with a solid form of a bioactive material, in particular a hydrogen peroxide generating material, such as sodium percarbonate, urea peroxide, and potassium percarbonate to form the bioactive complex. The introduction of the kit into water will cause the incorporation of the kit materials into the biocidal complex. This method has the advantage of being more compact and stable than aqueous solutions.

In further embodiments, the methods of minimizing premature degradation of bioactive material 202 for production are disclosed. Using temperature or dessication of the plant materials inactivates $H_2O_2$-degrading enzymes prior to exogenous $H_2O_2$ addition. Catalases and peroxidases are the primary $H_2O_2$-degrading catalysts that must be substantially inactivated from the plant material prior to combination with $H_2O_2$. Blanching of fresh plant matter or freezing/thawing of the fully hydrated plant cells or extended of heating solution with 1% or greater NaCl can also effectively inactivate enzymes.

Another aspect of the invention uses the above described inactivated $H_2O_2$-acting enzymes of the plant material as a method of capturing and stabilizing exogenously added $H_2O_2$ in a bioreactive form. Despite a great deal of research on their unique biochemical characteristics, very little is known about the catalytic mechanisms of oxalate oxidases, dismutases, peroxidases and catalases. Recently theories on catalytic mechanisms of $H_2O_2$ acting enzymes suggest three dimensional tunnel-like structures with some electrostatic guidance to the active site of a metal ion of Cu, Mn, or Zn. Minor perturbations in the three dimensional structure or absence of an enabling co-factor or monomer can render the enzyme functionally inactive or hypoactive but still capable of binding the hydrogen peroxide in a manner useful for the purposes of this invention.

Aqueous solutions of these plant materials combined with $H_2O_2$ exhibited increased bactericidal effectiveness of equivalent concentrations of aqueous plant extracts without exogenous $H_2O_2$ addition and extended duration than $H_2O_2$ alone. Test microbes were wild strain *Escherichia Coli*, *Escherichia Coli* ATCC 4352, *Staphylococcus aureus* ATCC 6538, *Psuedomonas aeruginosa* ATCC 9027, *Candida albicans* ATCC 10231, and *Aspergillis niger* ATCC 16404.

The present invention composed of various plant bases with $H_2O_2$ were challenged in-vitro with a range of microbial titrations in water. In 11 of 12 cases wild strain *E. coli* and *S. aureus* exhibited clean plate results down to single parts per billion concentrations with a shallow ramp in the time to complete kill vs dilution. Complete lack of survivors or rebound in the microbe population was observed until dilution reached a point of apparent depletion. The 150 µg/l composition from columnar cactus maintained 100% killing rate at 2 days and 7 days until 107 concentrations of *E. coli* were reached. At that inflection the slope of the concentration vs. survival curve looked similar to conventional free compounds, though still at several orders of magnitude lower concentration. The extended flat line of the clean plate dosage with the sudden steep transition from complete kill to survival is consistent with first order kinetics consistent with a "concentrated packet" behavior between the bacteria and the biocidal composition.

The composition proved only mycostatic on *Aspergillus niger*. The localized oxidative capacity of the reactive complexes tested was insufficient to overcome the considerable catalytic neutralization capacity of this exceptionally large eukaryote pathogen. However, absolute mycostasis at the bacteriostatic concentrations is consistent with the ability to overcome the smaller defense capacity of the *Aspergillus* buds. Bio-reactivity against virus, amoeba, and their cysts is consistent with the oxidative performance of hydrogen peroxide.

The plant materials 206 can be obtained from the tissues of most higher plants. The inventors have successfully produced the invention from plants of the families of Agavaceae, Cactaceae, Poaceae, Theaceae, Leguminosae and Lythraceae. However, the present invention is not limited to these families. Proper plants are able to be used in accordance with present invention. In some embodiment, plants that are generally regarded as safe by the U.S. FDA having a history of low toxicity are used.

An example is the cereal grains of the Poaceae family. Many plants in the family have a particularly high content of $H_2O_2$ acting compounds in the normally discarded grain sheaths and roots. Various species of Aloe, Pachycereus, and Opuntia were selected for initial testing because of their history in human food or folk medicinal use, characteristics consistent with xeric plants with high $H_2O_2$ defensive chemistry content, and availability without environmental, regulatory or cultivation concerns. Plants, such as these succulents, have structures adapted to retain a large quantity of water and asexually reproduce through stem/stalk cuttings. Their tissues have an abundance of distributed lignification ability and related $H_2O_2$ acting structures, such as peroxisomes and membrane proteins, that function in both defensive and growth processes. Seeds and fruits also exhibit the ability to withstand exceptional environmental stress in protecting germinating seedlings. Such adaptations are good indicators of the highly developed oxidative stress and pathogen management systems of these plants. A particularly environmentally durable $H_2O_2$-acting oxalate oxidase enzyme is commonly known as germin, a manganese containing homohexamer with both oxalate oxidase and superoxide dismutase activities. It is prevalent in seeds, buds, and sprouts to provide protections during the vulnerable germination phases. Cereal grains are noteworthy for containing a high concentration of germins in roots and seed membranes to protect the seeds and seedlings during germination. The discarded hulls of the seed germs are a potential source of tissue useful with this invention.

Regardless of the binding mechanism, the suitability and potency of a particular plant is affected by many species dependent, seasonal, and cultivation factors. One of the advantages of the present invention is the consistent level of potency that can be achieved by sub-saturation of the plant material binding sites. The addition of $H_2O_2$ at a molar quantity below the minimum baseline that the plant material can be assured to bind provides dose control and quality metrics that are rare in natural products.

Figure 3:
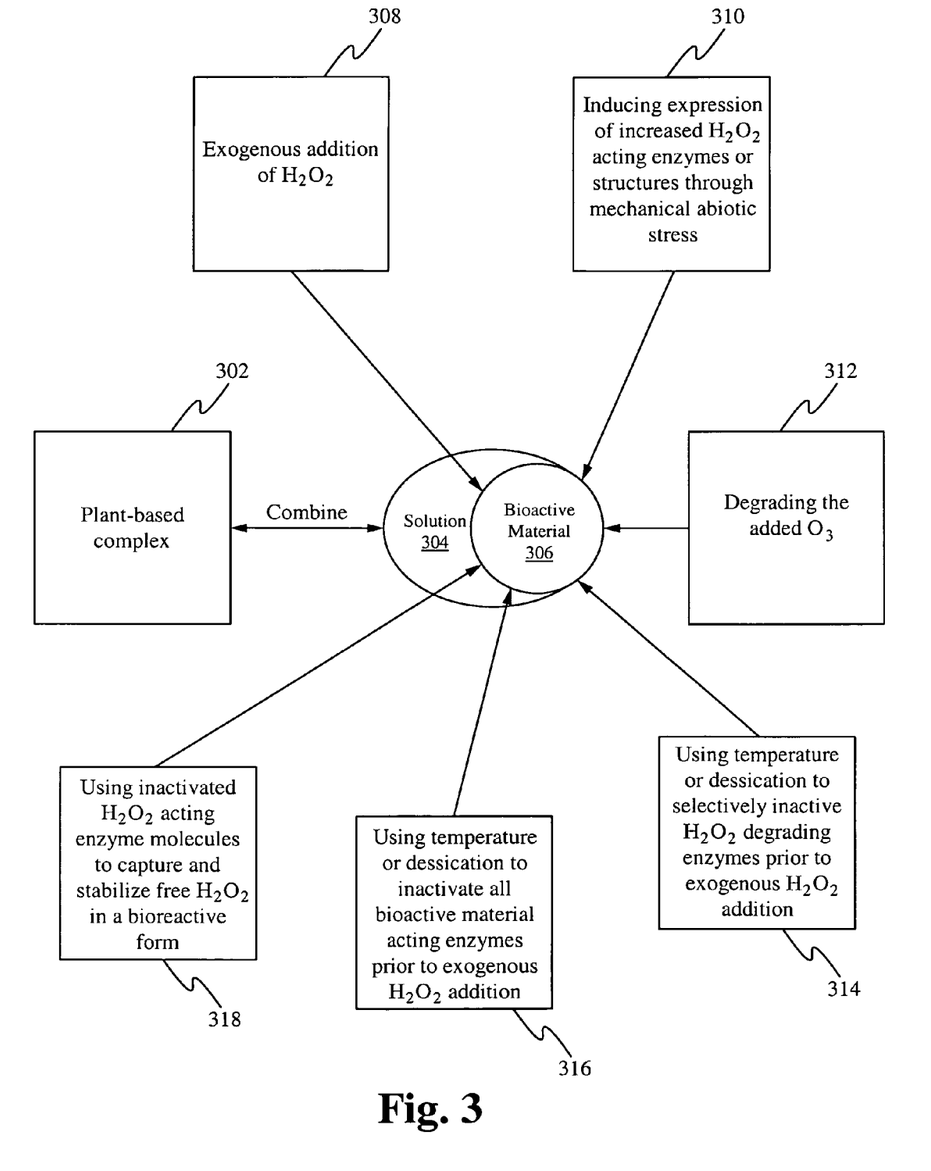

FIG. 3 illustrates a flow chart of a method of forming a plant-based biocidal solution of the present invention. The method of forming the plant-based biocidal solution of the present invention is achieved by combining a plant-based complex 302 with a solution 304 containing a bioactive material 306.

As described above, in some embodiments, the plant-based complex 302 and solution 304 can be prepared by the same method as preparing the plant-based complex 204 and solution 200, respectively. The bioactive material is added or generated by the same method described above. The methods of adding or generating the bioactive material, including but not limited to: (1) exogenous adding hydrogen peroxide 308; (2) inducing expression of increased $H_2O_2$ acting enzymes or structures through mechanical abiotic stress 310; (3) degrading the added ozone ($O_3$) by an active dismutase in the complex or solution, or in combination with direct adding of the $H_2O_2$ 312; (4) using temperature or dessication to selectively inactivate $H_2O_2$ degrading enzymes prior to exogenous $H_2O_2$ addition 314; (5) using temperature or dessication to inactivate all bioactive material acting enzymes prior to exogenous $H_2O_2$ addition 316; and (6) using inactivated $H_2O_2$ acting enzyme molecules to capture and stabilize free $H_2O_2$ in a bioreactive form 318.

Figure 4A:
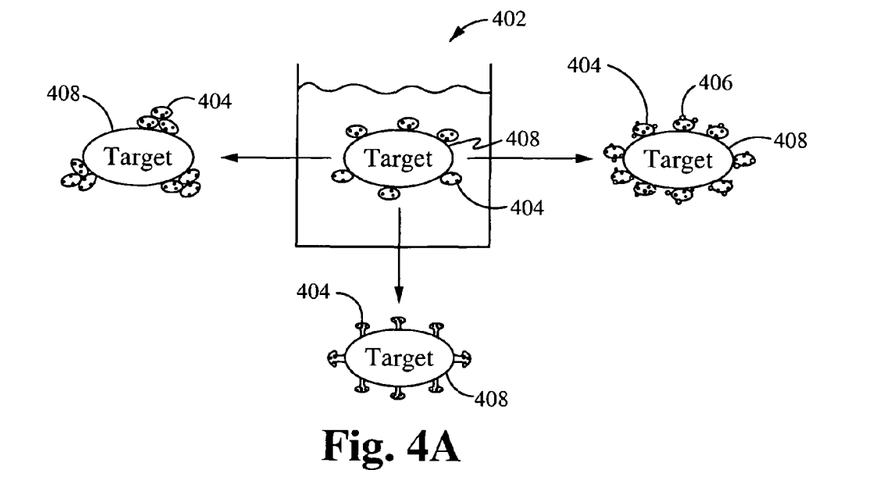
Figure 4B:
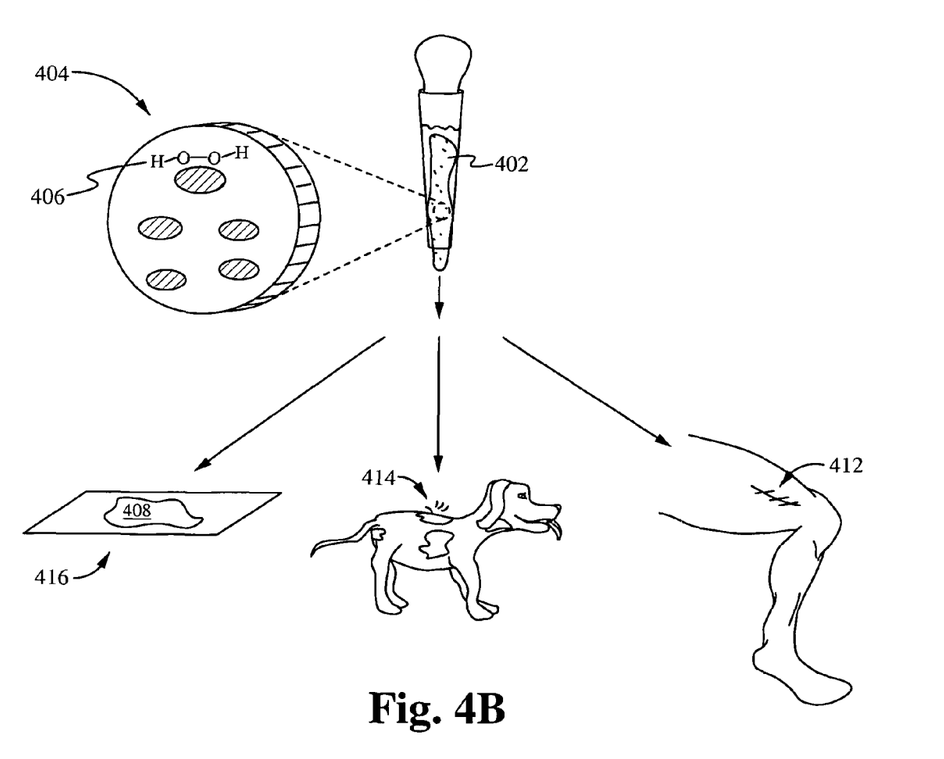

FIGS. 4A and 4B illustrate a use of plant-based biocidal solution of the present invention. The plant-based biocidal solution 402, containing a plant-based complex 404 binding bioactive material 406, can be applied to a target 408. In some embodiments, the plant-based biocidal solution can deliver high localized concentration of the bioactive material 406 to the target 408. In some embodiments, the target 408 can be a pathogen. In other embodiments, the plant-based biocidal solution 402 can have beneficial effect to human wound 412 or animal wound 414 healing.

Figure 5:
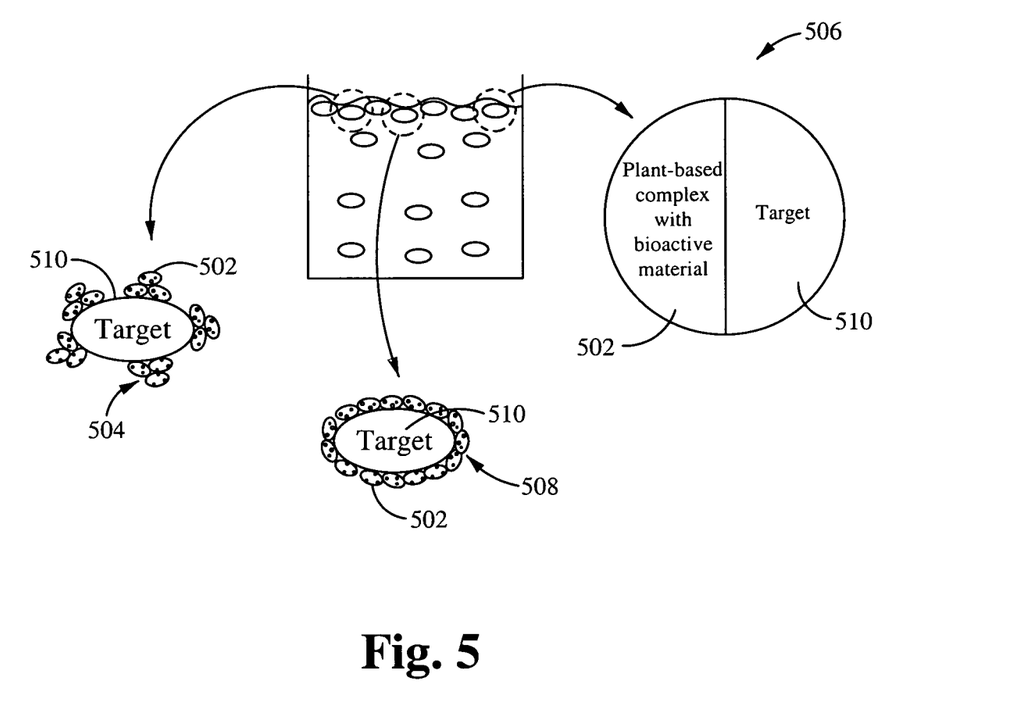

FIG. 5 illustrates another use of plant-based biocidal solution in the form of microscopic clusters, complexes, and aggregates of the present invention. The plant-based biocidal material 502 forms a microscopic cluster 504, a complex 506, or an aggregate 508 from a suspension of the plant-based complex. The plant-based biocidal material 502 can be applied to the target 510, thereby impairing the target 510.

Examples of Preparing the Composition:

One example of the preparation of the composition is as following: large pieces of stalk or leaves are harvested from live plants, de-spined and washed in cold water, and abiotic stress may optionally be induced by cutting the plant leaves or stalks into sufficiently large pieces to preserve sufficient local metabolic ability to express increased defensive enzyme structures. The pieces are then allowed to low-heat/air dessicate to inactivate the $H_2O_2$ degrading enzymes. Fine pulverization of the dried plant pieces increases solubility and disruption of cells to form fragments or subcellular particles. These cell fragments or particles contain both water soluble and non-water soluble forms of inactive materials, binding enzymes, potentially cooperating factors as well as potentially undesirable compounds. Water is used as the extraction medium for its $H_2O_2$ compatibility and to minimize undesirable non-water-soluble alkaloids, terpenes and the like that generally have higher toxicity than water soluble compounds. The pulverized plant materials are mixed in room temperature or heated water in the ratio of 100~20,000 water to 1 plant and allowed approximately 24 hours for dissolving of soluble materials. The liquid is passed through a 5 micron filter, then a concentration of 30-50% food grade $H_2O_2$ is added to the plant-water solution to make a final concentration of 0.05~3% of $H_2O_2$, preferably 1%, and allowed to react for one hour to promote cross-linking of proteins into aggregates. Additional food grade $H_2O_2$ with a concentration of 30-50% can be added to saturate available binding sites in the solution. The solution is allowed to react for a minimum 2 hours, preferably 8-24 hours. The solution is then diluted to reduce the introduced $H_2O_2$ content to 0.02%, a level at which the unbound $H_2O_2$ will degrade spontaneously within a few days. The composition is diluted to desired commercial concentration and packaged.

Standard methods are used to evaluate and indicate specific minimum biocidal potency and $H_2O_2$ content. The solution is sampled and diluted to a concentration of 100 parts per billion.

Method 1: challenged with a solution of 106/ml indicator bacteria culture. The plates must show zero colonies after 12 hours.

Method 2: the $H_2O_2$ may be also tested using catalase treated filter paper. The treated disk is submerged in standard diluted solution and the disk must become buoyant in less than specified time.

Method 3: the use of commercially available hydrogen peroxide test strips provide colorimetric indication of bioactive hydrogen peroxide content.

The term binding or its equivalents are used to illustrate the interactions between or among molecules. The interactions include chemical bonds and physical forces. For example, covalent interactions, ionic interactions, Van der Waals interactions, electrostatic or hydrogen bonds, reversible and irreversible chemical reactions, oxidation and reduction reactions, or other proper forces and reactions.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the appended claims.

What is claimed is:

1. A multi-component, antibacterial composition consisting of a product prepared by a process having the steps of:
    combining green tea leaves with water and substantially inactivating hydrogen peroxide degrading enzymes endogenous to the green tea leaves using heat, to create a first mixture;
    combining pomegranate husk with water and substantially inactivating hydrogen peroxide degrading enzymes endogenous to the pomegranate husk using heat, to create a second mixture;
    combining the first mixture with the second mixture and adding hydrogen peroxide;
    wherein the antibacterial composition comprises a percentage of hydrogen peroxide selected from 0.05 to 3%, 1% or 0.02%.

2. The multi-component, antibacterial composition of claim 1, wherein the composition comprises 1% of hydrogen peroxide.

3. An antibacterial composition consisting of a product prepared by a process having the steps of:
    combining pomegranate husk with water and substantially inactivating hydrogen peroxide degrading enzymes endogenous to the pomegranate husk using heat, to create a mixture and adding hydrogen peroxide to the mixture;
    wherein the antibacterial composition comprises a percentage of hydrogen peroxide selected from 0.05 to 3%, 1% or 0.02%.

4. The antibacterial composition of claim 1, wherein the antibacterial composition comprises 0.05 to 3% of hydrogen peroxide.

5. The antibacterial composition of claim 1, wherein the antibacterial composition comprises 0.02% of hydrogen peroxide.

6. A dry form of the antibacterial composition of claim 1.

7. The antibacterial composition of claim 3, wherein the composition comprises 1% of hydrogen peroxide.

8. The antibacterial composition of claim 7, wherein the antibacterial composition comprises 0.05 to 3% of hydrogen peroxide.

9. The antibacterial composition of claim 7, wherein the antibacterial composition comprises 0.02% of hydrogen peroxide.

10. The antibacterial composition of claim 4, wherein the antibacterial composition comprises 1% of hydrogen peroxide.

11. A dry form of the antibacterial composition of claim 7.

* * * * *